US011351378B2

(12) United States Patent
Grill et al.

(10) Patent No.: US 11,351,378 B2
(45) Date of Patent: Jun. 7, 2022

(54) METHOD TO DESIGN TEMPORAL PATTERNS OF NERVOUS SYSTEM STIMULATION

(71) Applicant: DUKE UNIVERSITY, Durham, NC (US)

(72) Inventors: Warren M. Grill, Chapel Hill, NC (US); David T. Brocker, Cary, NC (US); Alexander R. Kent, Durham, NC (US)

(73) Assignee: DUKE UNIVERSITY, Durham, NC (US)

(*) Notice: Subject to any disclaimer, the term of this patent is extended or adjusted under 35 U.S.C. 154(b) by 189 days.

(21) Appl. No.: 16/472,466

(22) PCT Filed: Dec. 21, 2017

(86) PCT No.: PCT/US2017/067878

§ 371 (c)(1),
(2) Date: Jun. 21, 2019

(87) PCT Pub. No.: WO2018/119220

PCT Pub. Date: Jun. 28, 2018

(65) Prior Publication Data

US 2021/0128920 A1 May 6, 2021

Related U.S. Application Data

(60) Provisional application No. 62/437,356, filed on Dec. 21, 2016.

(51) Int. Cl.
*A61N 1/36* (2006.01)
*G16H 20/30* (2018.01)
(Continued)

(52) U.S. Cl.
CPC ....... *A61N 1/36139* (2013.01); *A61N 1/3606* (2013.01); *A61N 1/36067* (2013.01);
(Continued)

(58) Field of Classification Search
CPC ................ A61N 1/0534; A61N 1/3606; A61N 1/36067; A61N 1/36075; A61N 1/36171;
(Continued)

(56) References Cited

U.S. PATENT DOCUMENTS

2010/0121407 A1 5/2010 Pfaff
2010/0016280 A1 6/2010 Grill et al.
(Continued)

OTHER PUBLICATIONS

European Patent Office, Extended European Search Report for EP Pat. App. 17883046, dated Jun. 19, 2020.
(Continued)

*Primary Examiner* — Jon Eric C Morales
(74) *Attorney, Agent, or Firm* — McDonald Hopkins LLC

(57) ABSTRACT

The present invention relates to methods that enable one to design temporal patterns for the optimal stimulation of a nervous system, one or more nerve cells, or nervous tissue. In one embodiment, the present invention relates to methods to design improved stimulation patterns and/or genetic algorithms for the optimal stimulation of a nervous system, one or more nerve cells, or nervous tissue. In one embodiment, the present invention utilizes a model-based design to achieve a more optimal stimulation pattern for use in connection with a nervous system, one or more nerve cells, or nervous tissue (e.g., a human nervous system). In another embodiment, the model-based design of the present invention utilizes a systematic search method to identify parameters (e.g., design variables) that minimize a cost function (e.g., optimize the fitness of a particular design). In one instance, the system and method of the present invention is demonstrated via optimal temporal patterns of electrical
(Continued)

stimulation for a nervous system, one or more nerve cells, or nervous tissue.

27 Claims, 14 Drawing Sheets

(51) Int. Cl.
*G16H 50/50* (2018.01)
*G16B 5/20* (2019.01)

(52) U.S. Cl.
CPC ..... *A61N 1/36075* (2013.01); *A61N 1/36132* (2013.01); *A61N 1/36171* (2013.01); *G16B 5/20* (2019.02); *G16H 20/30* (2018.01); *G16H 50/50* (2018.01)

(58) Field of Classification Search
CPC ........... A61N 1/36139; A61N 1/36132; G16H 20/30; G16H 50/50; G16H 50/70; G06N 3/049
See application file for complete search history.

(56) References Cited

U.S. PATENT DOCUMENTS

2014/0350634 A1* 11/2014 Grill ........................ A61B 5/24 607/45
2015/0127066 A1* 5/2015 Grill, Jr. ............ A61N 1/36082 607/59
2016/0022993 A1 1/2016 Grill
2018/0064943 A1* 3/2018 Grill .................. A61N 1/36062

OTHER PUBLICATIONS

"Optimized temporal pattern of brain stimulation designed by computational evolution" (Brocker, DT et al.) Science Translational Medicine. Jan. 4, 2017. vol. 9, issue 371. pp. 2,7.
"Improved Efficacy and Efficiency of Non-Regular Temporal Patterns of Deep Brain Stimulation for Parkinson's Disease" (Brocker, DT) issue date Jan. 2015. pp. 58, 74-75, 77, 79, 85-86, 91-92, 169, 220.
"Time and Frequency-Dependent Modulation of Local Field Potential Synchronization by Deep Brain Stimulation" (McCracken, CB et al.) Jul. 16, 2014. PLOS ONE. vol. 9, Issue 7. p. 3.
"Capturing with EEG the Neural Entrainment and Coupling Underlying Sensorimotor Synchronization to the Beat" (Nozaradan, Set al.) Oct. 9, 2013. Cerebral Cortex. Mar. 2015 issue. vol. 25. pp. 736-747.
"High Frequency Deep Brain Stimulation in the Hippocampus Modifies Seizure Characteristics in Kindled Rats" (Wyckhuys, T et al.) Aug. 2008. Epilepsia. vol. 48. No. 9. p. 1545.
International Search Report and Written Opinion dated Feb. 23, 2018; International Patent Application No. PCT/US2017/067878 filed Dec. 27, 2017.

* cited by examiner

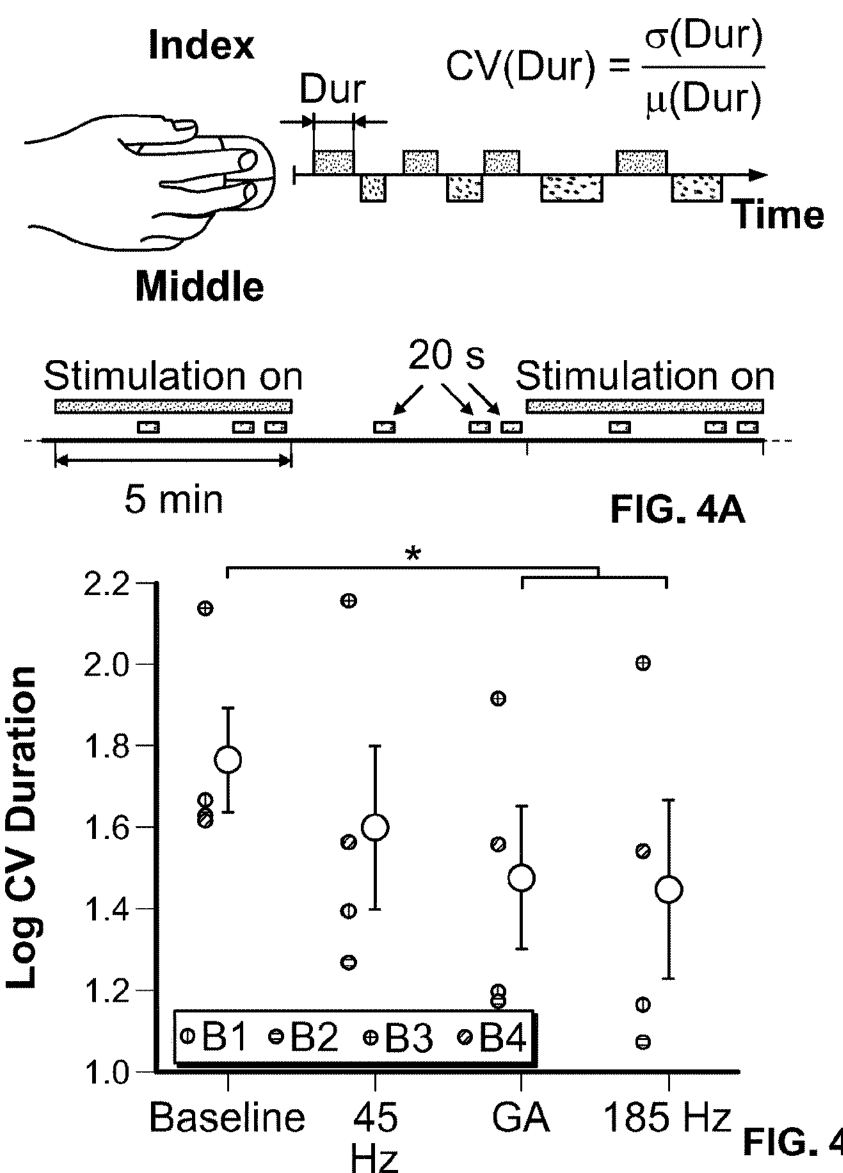
FIG. 4A
FIG. 4C
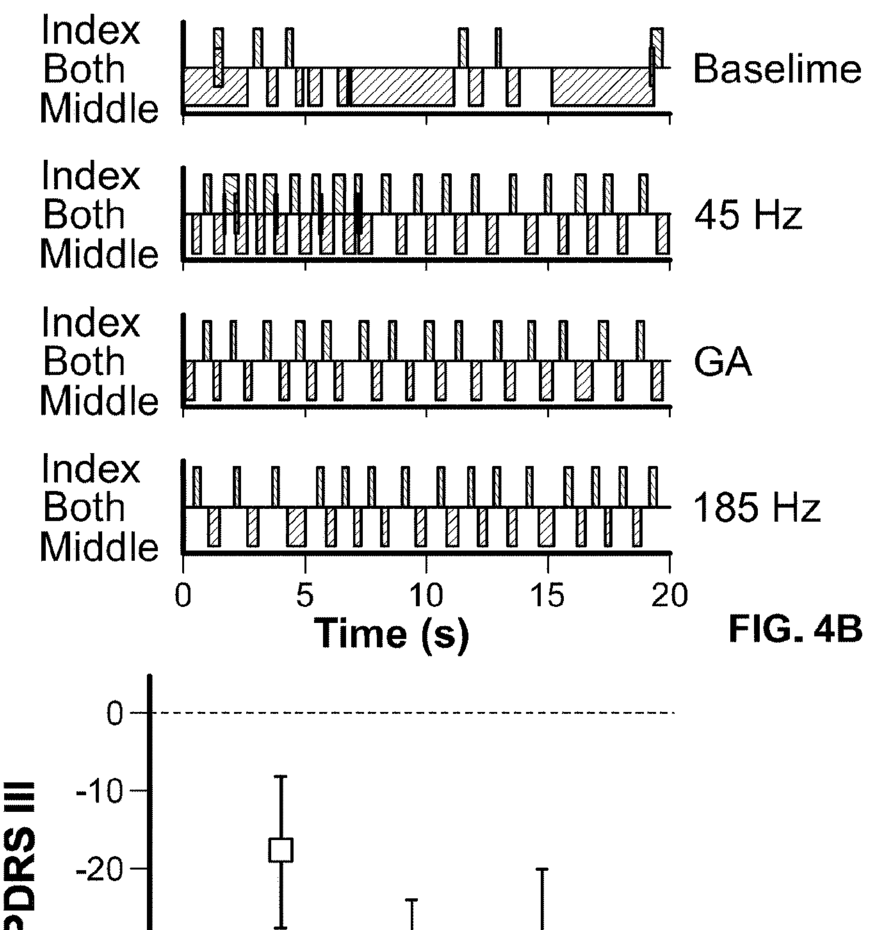
FIG. 4B
FIG. 4D

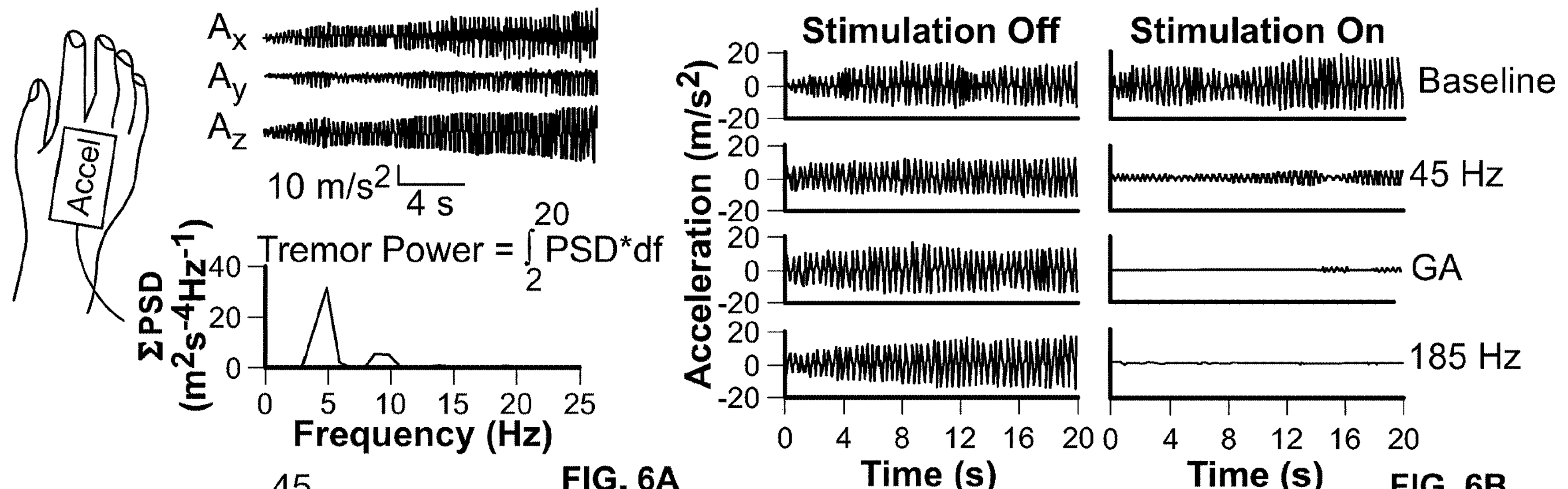
FIG. 6A
FIG. 6C
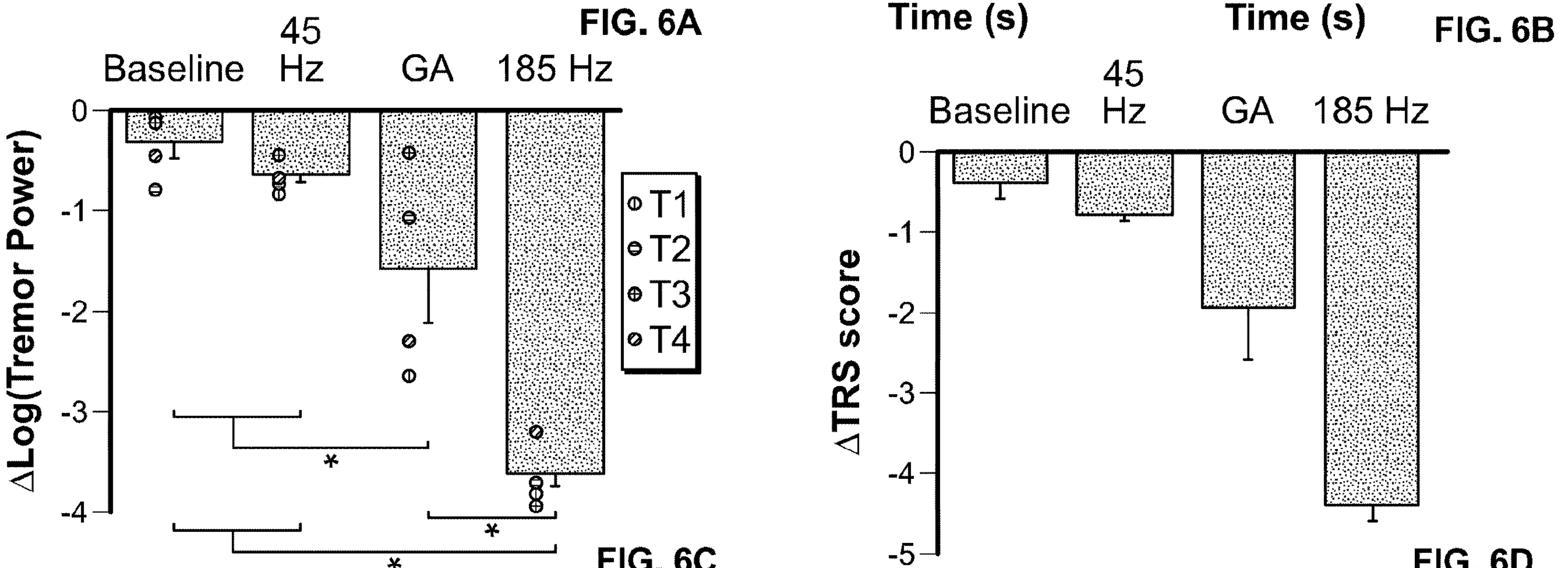
FIG. 6B
FIG. 6D

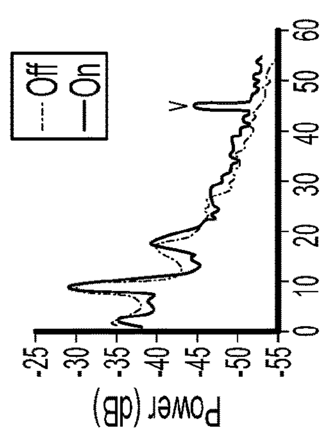
FIG. 7A
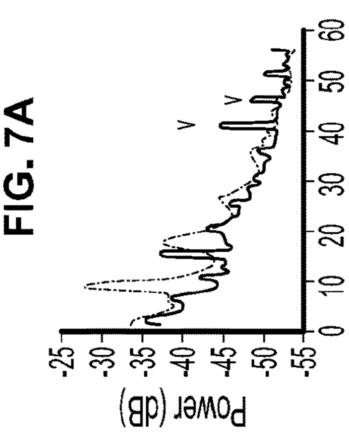
FIG. 7B
FIG. 7C
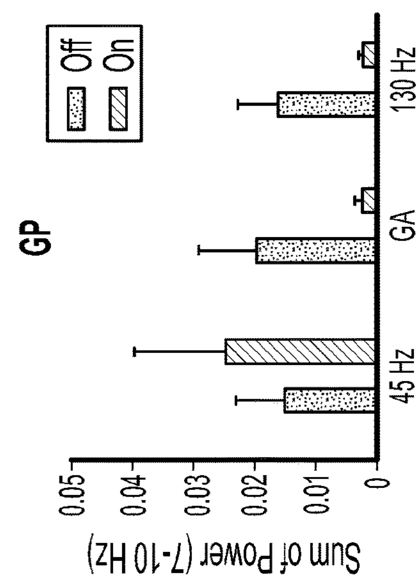
FIG. 7D
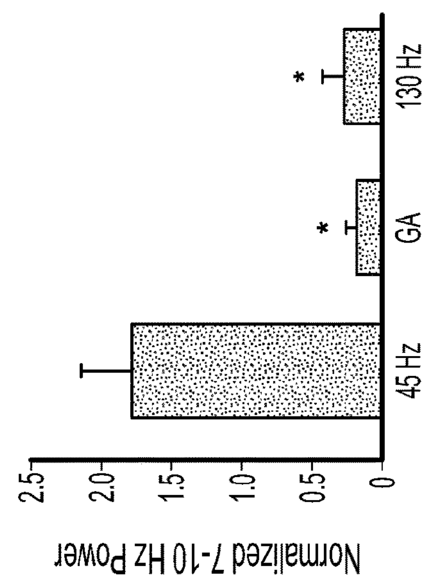
FIG. 7E
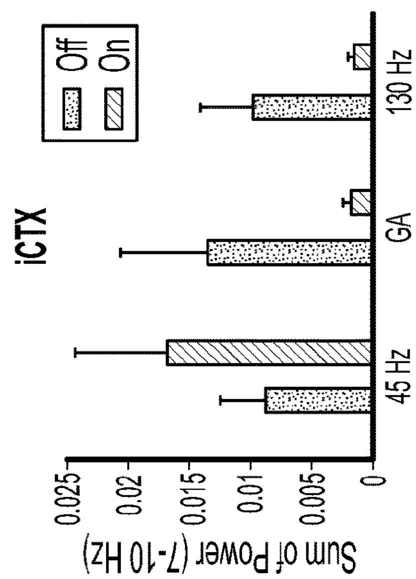
FIG. 7F
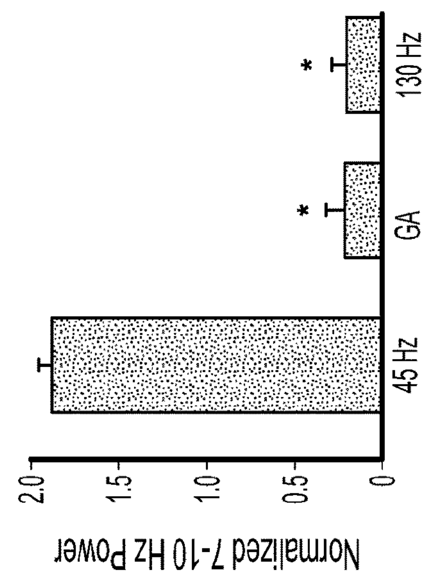
FIG. 7G

METHOD TO DESIGN TEMPORAL PATTERNS OF NERVOUS SYSTEM STIMULATION

RELATED APPLICATION DATA

This application is a 35 U.S.C. 371 national stage filing of PCT Application No. PCT/US2017/067878 filed on Dec. 21, 2017, which claims priority to and is a non-provisional of U.S. Provisional Patent Application No. 62/437,356 filed Dec. 21, 2016 and entitled "Optimized Temporal Pattern of Brain Stimulation Designed by Computational Evolution," each of which are hereby incorporated herein by reference in their entirety.

GOVERNMENT RIGHTS STATEMENT

This invention was made with Government support under Federal Grant No. R37 NS040894 awarded by the NIH. The Federal Government has certain rights in this invention.

FIELD OF THE INVENTION

The present invention relates to methods that enable one to design temporal patterns for the optimal stimulation of the nervous system, one or more nerve cells, or nervous tissue. In one embodiment, the present invention relates to methods to design improved stimulation patterns and/or genetic algorithms for the optimal stimulation of a nervous system, one or more nerve cells, or nervous tissue. In one embodiment, the present invention utilizes a model-based design to achieve a more optimal stimulation pattern for use in connection with a nervous system, one or more nerve cells, or nervous tissue (e.g., a human nervous system). In another embodiment, the model-based design of the present invention utilizes a systematic search method to identify parameters (e.g., design variables) that minimize a cost function (e.g., optimize the fitness of a particular design). In one instance, the system and method of the present invention is demonstrated via a genetic algorithm designed to achieve optimal temporal patterns of electrical stimulation of the nervous system, one or more nerve cells, or nervous tissue.

BACKGROUND OF THE INVENTION

A genetic algorithm (GA) is a high dimensional search algorithm that emulates evolutionary biology to find an optimal solution. GAs take advantage of the effects of natural selection, reproduction, migration, and mutation to identify solutions that minimize an associated cost function. GA-based optimization has been successfully applied to a wide variety of problems, including robotic navigation, pattern recognition, speech recognition, and engineering design of circuits.

One potential non-limiting application for GA-based optimization is for brain stimulation in the instance of patient's with Parkinson's disease (PD). As is well known, PD is a progressive, neurodegenerative disease characterized by motor symptoms that include bradykinesia, resting tremor, postural instability, and rigidity. Although dopamine replacement therapy treats the symptoms of PD, long-term use is complicated by the requirement for higher and more frequent dosing, motor fluctuations, and dyskinesias. Deep brain stimulation (DBS) is an effective and adjustable surgical treatment for advanced PD that improves motor symptoms, improves quality of life, and reduces motor fluctuations. However, this therapy has not been optimized, and there have been few improvements in DBS since its introduction.

The stimulation parameters used for DBS are determined empirically and consist of short-duration (about 60 to about 180 μs), high-frequency (typically about 130 to about 185 Hz) pulses of electrical stimulation to ameliorate symptoms. The efficacy of DBS is strongly dependent on the frequency of stimulation: low-frequency stimulation (less than about 50 Hz) is ineffective or exacerbates symptoms, while high-frequency stimulation produces symptomatic benefit. Nevertheless, high stimulation frequencies can cause stronger side effects and consume more energy than low frequency stimulation, leading to frequent surgical replacement of battery-powered, implanted pulse generators (IPGs). IPG replacement surgeries are expensive and carry risks, including infection and miss-programming.

Present DBS systems deliver a regular temporal pattern of stimulation; inter-pulse intervals do not vary as a function of time. Irregular temporal patterns of stimulation have been used in animal and human studies to probe DBS mechanisms. Random patterns of DBS, even when delivered at a high average frequency, are not effective in ameliorating parkinsonian symptoms in rats, tremor in persons with essential tremor or bradykinesia in patients with PD. These results indicate that the effects DBS on symptoms are strongly dependent on the temporal pattern of stimulation and motivated our current study in which we sought to design a temporal pattern for DBS that would be more efficient than conventional high-frequency DBS.

Accordingly, there is a need in the art for an improved method for the design of improved or optimized temporal patterns for the optimal stimulation of a nervous system, one or more nerve cells, or nervous tissue and most specifically related to the design of improved non-regular temporal patterns.

SUMMARY OF THE INVENTION

The present invention relates to methods that enable one to design improved temporal patterns for the optimal stimulation of a nervous system, one or more nerve cells, or nervous tissue. In one embodiment, the present invention relates to methods to design improved stimulation patterns for the optimal stimulation of a nervous system, one or more nerve cells, or nervous tissue. In one embodiment, the present invention utilizes a model-based design to achieve a more optimal stimulation pattern for use in connection with a nervous system, one or more nerve cells, or nervous tissue (e.g., a human nervous system). In another embodiment, the model-based design of the present invention utilizes a systematic search method to identify parameters (e.g., design variables) that minimize a cost function (e.g., optimize the fitness of a particular design). In one instance, the system and method of the present invention is demonstrated via design of optimal temporal patterns of electrical stimulation for a nervous system, one or more nerve cells, or nervous tissue.

In one embodiment, the present invention provides systems and methods for the use of model-based computational evolution to design temporal pattern of stimulation that reduces the average stimulation frequency of DBS and preserved efficacy.

In another embodiment, the present invention provides systems and methods that utilize low frequency non-regular patterns of deep brain stimulation for the treatment of symptoms of neurological disorders. In some embodiments, the non-regular temporal pattern of stimulation comprises a sequence of electrical pulses delivered to one or more neural tissues, the intervals between pulses (i.e., the inter-pulse intervals) can vary from one pulse to the next. In other embodiments, the low frequency comprises less than about 100 Hz.

In still another embodiment, the present invention provides a device and methods for obtaining neural recordings during non-regular patterns of brain stimulation using a time-domain solution. In some embodiments, the device comprises an implantable pulse generator that is capable of generating and delivering non-regular patterns of stimulation while simultaneously recording neural activity. In other embodiments, the implantable pulse generator uses an amplifier-blanking paradigm that briefly grounds the inputs during a short period encompassing the stimulation pulse, thereby preventing the violation of the input specifications of the amplifiers (railing the amplifiers), and the short gaps in the data can be overcome with real-time or post-processing analysis. In various non-limiting embodiments, the neurological disorder addressed comprises a neurological disease. In certain non-limiting embodiments, the neurological disease comprises Parkinson's disease.

Accordingly, in one embodiment the present invention is drawn to a method for achieving neural stimulation comprising the steps of: (A) selecting a neural model based on the nature of a disease to be treated or a neurological stimulation to be achieved; (B) using the selected neural model to design a stimulation pattern; and (C) stimulating one or more neurons or one or more neural tissues in an individual using the stimulation pattern designed in Step (B) using a stimulation device.

In still another embodiment, the present invention is drawn to a method for designing an improved neural stimulation device, the method comprising the steps of: providing a neural stimulation device that comprises a pulse-based stimulation pattern designed by model-based optimization.

The various features of novelty which characterize the invention are pointed out with particularity in the claims annexed to and forming a part of this disclosure. For a better understanding of the invention, its operating advantages and specific benefits attained by its uses, reference is made to the accompanying drawings and descriptive matter in which exemplary embodiments of the invention are illustrated.

BRIEF DESCRIPTION OF THE DRAWINGS

The present teachings may be better understood by reference to the following detailed description taken in connection with the following illustrations, wherein:

FIGS. 4A through 4D illustrate the effects of temporal patterns of STN DBS on bradykinesia in persons with PD;

FIGS. 6A through 6D illustrate the effects of temporal patterns of STN DBS on tremor in persons with PD;

FIGS. 7A through 7G illustrate the effect of temporal pattern of STN DBS on low-frequency oscillations in the globus pallidus (GP) and ipsilateral cortex (iCTX) of hemi-parkinsonian rats;

DETAILED DESCRIPTION OF THE INVENTION

Figure 1A:
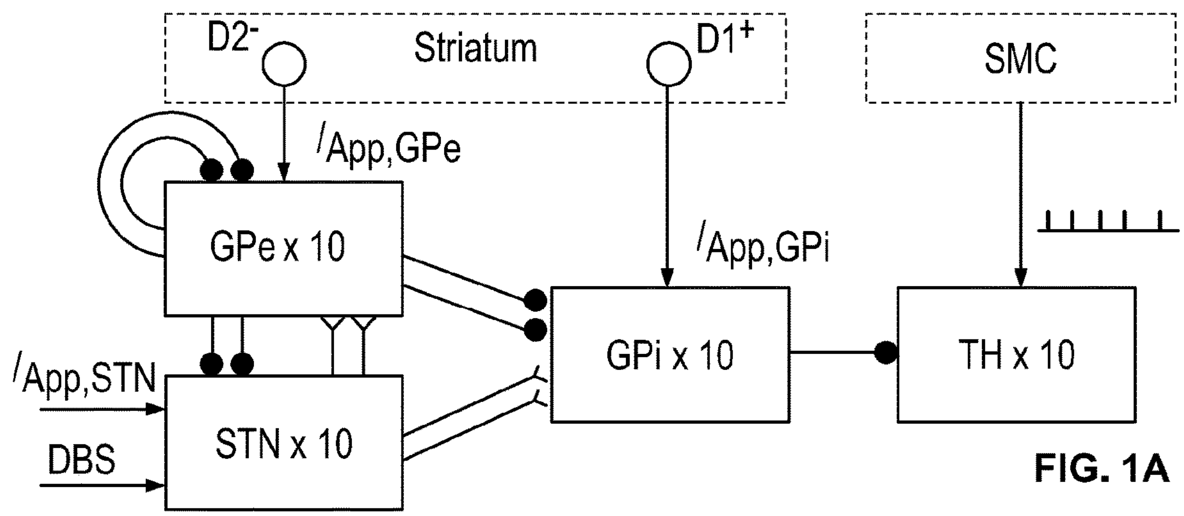
FIGS. 1A through 1F illustrate various aspects of model-based design by computational evolution of an optimized temporal pattern of DBS.

Reference will now be made in detail to exemplary embodiments of the present teachings, examples of which are illustrated in the accompanying drawings. It is to be understood that other embodiments may be utilized and structural and functional changes may be made without departing from the respective scope of the present teachings. Moreover, features of the various embodiments may be combined or altered without departing from the scope of the present teachings. As such, the following description is presented by way of illustration only and should not limit in any way the various alternatives and modifications that may be made to the illustrated embodiments and still be within the spirit and scope of the present teachings.

As used herein, the words "example" and "exemplary" mean an instance, or illustration. The words "example" or "exemplary" do not indicate a key or preferred aspect or embodiment. The word "or" is intended to be inclusive rather an exclusive, unless context suggests otherwise. As an example, the phrase "A employs B or C," includes any inclusive permutation (e.g., A employs B; A employs C; or A employs both B and C). As another matter, the articles "a" and "an" are generally intended to mean "one or more" unless context suggests otherwise. By way of example, "an element" means at least one element and can include more than one element. Unless otherwise defined, all technical terms used herein have the same meaning as commonly understood by one of ordinary skill in the art to which this disclosure belongs.

It is noted that the various embodiments described herein may include other components and/or functionality. It is further noted that while various embodiments refer to treatment of a specific condition, symptom or disease, various other conditions, symptoms and diseases may be treated in view of embodiments described herein. For example, embodiments may be utilized in treating Parkinson's disease, essential tremor or the like within the brain of a patient. However, the present teachings may be applied more broadly to any kind of condition, symptom and disease treated using electrical stimulation. This may include utilizing the disclosed embodiments to develop non-regular temporal patterns of electrical stimulation that are then applied to treat pain, applying electrical stimulation for occipital nerve stimulation such as to treat headaches, applying stimulation for rehabilitation of a body component, etc. The embodiments disclosed are merely exemplary and are not intended to be exhaustive.

As noted above, the present invention relates to methods that enable one to design temporal patterns for the optimal stimulation of a nervous system, one or more nerve cells, or nervous tissue, including, without limitation non-regular temporal patterns of stimulation. In one embodiment, the present teachings relate to methods to design improved stimulation patterns for the optimal stimulation of a nervous system, one or more nerve cells, or nervous tissue. In one embodiment, the present invention utilizes a model-based design to achieve a more optimal stimulation pattern for use in connection with a nervous system, one or more nerve cells, or nervous tissue (e.g., a human nervous system). In another embodiment, the model-based design of the present teaching utilizes a systematic search method to identify parameters (e.g., design variables) that minimize a cost function (e.g., optimize the fitness of a particular design). In one instance, the system and method of the present invention is demonstrated via design of optimal temporal patterns of electrical stimulation for a nervous system, one or more nerve cells, or nervous tissue.

In one embodiment, the present invention provides systems and methods for the use of model-based computational evolution to design temporal pattern of stimulation that reduces the average stimulation frequency of DBS and preserved efficacy, which can improve the overall efficiency of the system.

In another embodiment, the present invention provides systems and methods that utilize low frequency non-regular patterns of deep brain stimulation for the treatment of symptoms of neurological disorders. In some embodiments, the non-regular temporal pattern of stimulation comprises a sequence of electrical pulses delivered to one or more neural tissues, the intervals between pulses (i.e., the inter-pulse intervals) can vary from one pulse to the next. In other embodiments, the low frequency comprises less than about 100 Hz.

In still another embodiment, the present invention provides a device and methods for obtaining neural recordings during non-regular patterns of brain stimulation using a time-domain solution. In some embodiments, the device comprises an implantable pulse generator that is capable of generating and delivering non-regular patterns of stimulation while simultaneously recording neural activity. In other embodiments, the implantable pulse generator uses an amplifier-blanking paradigm that briefly grounds the inputs during a short period encompassing the stimulation pulse, thereby preventing the violation of the input specifications of the amplifiers (railing the amplifiers), and the short gaps in the data can be overcome with real-time or post-processing analysis. In various non-limiting embodiments, the neurological disorder addressed comprises a neurological disease. In certain non-limiting embodiments, the neurological disease comprises Parkinson's disease.

As also noted above, a genetic algorithm (GA) is a high dimensional search algorithm that emulates evolutionary biology to find an optimal solution. GAs take advantage of the effects of natural selection, reproduction, migration, and mutation to identify solutions that minimize an associated cost function. GA-based optimization has been successfully applied to a wide variety of problems, including robotic navigation, pattern recognition, speech recognition, and engineering design of circuits. However, current GAs suffer from a variety of issues when applied to various design challenges such as, but not limited to, the design of temporal patterns for neural stimulation applications.

Accordingly, in one embodiment, the present invention is directed to a method to achieve the design of improved genetic algorithms (GAs) that permit the design of optimized items such as optimized temporal patterns for the stimulation of a nervous system, one or more nerve cells, or nervous tissue. It should be noted that the present invention is not limited to just one end use and/or design application (i.e., the design of temporal patterns for the stimulation of a nervous system, one or more nerve cells, or nervous tissue). Rather, the methods disclosed herein can be broadly applied to a wide range of design challenges where the design of improved genetic algorithms are desired and/or needed.

In one instance, the present invention incorporates the use of non-regular temporal patterns for stimulation that have the potential to be applied to many forms of electrical stimulation including, but not limited to, spinal cord stimulation, deep brain stimulation, etc.

In light of the above, one method to determine the best stimulation pattern is to assign a binary vector to represent a desired stimulation pattern where each of the binary numbers will represent a time period of 1 ms. A 200 ms repeating pattern would thus have $2^{200}=1.6\times10^{60}$ possible combinations. As such, the present invention uses a highly efficient search method to identify the optimum stimulation pattern.

Given the above, for the purposes of promoting an understanding of the principles of the present invention reference will now be made to various embodiments and specific language will be used to describe the same. It will nevertheless be understood that no limitation of the scope of the disclosure is thereby intended, such alteration and further modifications of the disclosure as illustrated herein, being contemplated as would normally occur to one skilled in the art to which the disclosure relates.

As used herein, the term "subject" and "patient" are used interchangeably herein and refer to both human and nonhuman animals. The term "nonhuman animals" of the disclosure includes all vertebrates, e.g., mammals and non-mammals, such as nonhuman primates, sheep, dog, cat, horse, cow, chickens, amphibians, reptiles, and the like. Preferably, the subject is a human patient.

The systems and methods of the present invention can be used in the treatment, prevention, amelioration, and/or management of many disorders of the nervous system, including but not limited to, (i) neurodegenerative diseases such as Alzheimer's disease, Parkinson's disease, Huntington's disease and Multiple Sclerosis (MS), amyotrophic lateral sclerosis (ALS or Lou Gehrig's disease); (ii) CNS involvement in Hunter syndrome, mitochondrial encephalopathies, cerebrovascular disease (e.g. stroke; restenosis; cerebral ischemia; intracranial aneurysms, subarachnoid hemorrhage, and vasospasm); (iii) psychiatric illnesses such as anxiety, depression, schizophrenia, and sleep disorders; (iv) disorders of memory/cognition; (v) epilepsy; (vi) pain (considered to be a neurological disorder); (vii) migraine; (vii) spasticity; (vii) brain tumors (e.g., malignant gliomas); (viii) physical trauma (e.g., traumatic brain injury, spinal cord injury and other CNS injury); and (ix) vasospasm.

The following examples are provided by way of illustration and not by way of limitation.

EXAMPLES

Optimized Temporal Pattern of Stimulation Designed by Computational Evolution:

Brain stimulation is a promising therapy for several neurological disorders, including Parkinson's disease. Electrical stimulation, however, can also be used to treat many other disorders, diseases and symptoms. These may include, without limitation, applying electrical stimulation to treat pain (in any part of the body), mental disorders, incontinence, headaches, to rehabilitate a patient and the like. Stimulation parameters are selected empirically and are limited to the frequency and intensity of stimulation. The present invention utilizes a temporal pattern of stimulation as a novel parameter of deep brain stimulation to ameliorate symptoms in a parkinsonian animal model and in humans with Parkinson's disease along with other diseases, symptoms, and disorders. Further, it should be understood that while deep brain stimulation is discussed throughout the application, the present teachings and invention may be applied to any kind of electrical stimulation, including, without limitation, electrical stimulation using an ex-vivo electrical stimulator. The present teachings contemplate both implantable pulse generators and pulse generators utilized outside of a body. The pulse generator may include a processor to which applies a non-regular pulse train. Further, the pulse generator may include a memory in communication with the processor to store the applicable or a plurality of pulse trains. The present teachings contemplate any kind of pulse generator. Additionally, the present invention utilizes model-based computational evolution to optimize the stimulation pattern through utilization of an improved cost function. The optimized pattern produces symptom relief comparable to that from standard high-frequency stimulation (a constant rate of 130 or 185 Hz) and outperforms frequency-matched standard stimulation in the parkinsonian rat and in patients, for example. Both optimized and standard stimulation suppress abnormal oscillatory activity in the basal ganglia of rats and humans. The results of the present teachings illustrate the utility of model-based computational evolution to design temporal pattern of stimulation utilizing the improved cost function to increase the efficiency of brain stimulation in Parkinson's disease (and any other disease, disorder or symptom) thereby requiring substantially less energy than traditional brain stimulation and/or resulting in more efficacious treatment.

It should be noted that while PD is described throughout, it is merely exemplary and that the present teachings can apply to any kind of treatment of a disease, symptom, disorder and/or to rehabilitate a patient through electrical stimulation. The electrical stimulation contemplated can be any kind of stimulation, including, without limitation electrical stimulation through an implanted pulse generator, a pulse generator positioned ex-vivo with a lead and/or electrode positioned in-vivo, or any combination of such. Further still, the present teachings could apply to a TENS system.

As noted above, PD is a progressive, neurodegenerative disease characterized by motor symptoms that include bradykinesia, resting tremor, postural instability, and rigidity. Although dopamine replacement therapy treats the symptoms of PD, long-term use is complicated by the requirement for higher and more frequent dosing, motor fluctuations, and dyskinesias. Deep brain stimulation (DBS) is an effective and adjustable surgical treatment for advanced PD that improves motor symptoms, improves quality of life, and reduces motor fluctuations. However, this therapy has not been optimized, and there have been few improvements in DBS since its introduction.

The stimulation parameters used for DBS are determined empirically and generally consist of short-duration (e.g., about 60 to about 180 μs), high-frequency (typically about 130 about 185 Hz) pulses of electrical stimulation to ameliorate symptoms. The efficacy of DBS is strongly dependent on the frequency of stimulation: low-frequency stimulation (less than about 50 Hz) is typically ineffective or exacerbates symptoms, while high-frequency stimulation produces symptomatic benefit. Nevertheless, high stimulation frequencies can cause stronger side effects and consume more energy than low frequency stimulation, leading to frequent surgical replacement of battery-powered, implanted pulse generators (IPGs). IPG replacement surgeries are expensive and carry risks, including infection and miss-programming.

Present DBS systems deliver a regular temporal pattern of stimulation; inter-pulse intervals do not vary as a function of time. Irregular temporal patterns of stimulation have been used in animal and human studies to probe DBS mechanisms, such as those disclosed in U.S. Pat. No. 8,447,405, which is incorporated herein by reference. Random patterns of DBS, even when delivered at a high average frequency, are not effective in ameliorating parkinsonian symptoms in rats, tremor in persons with essential tremor or bradykinesia in patients with PD or at least not as effective as is possible. These results indicate that the effects DBS on symptoms are strongly dependent on the temporal pattern of stimulation and motivated the present invention in which the inventors sought to design a temporal pattern for DBS that would be more efficient and/or effective than conventional high-frequency DBS.

Design of Optimized Temporal Pattern of Stimulation with Computational Evolution:

The present teachings utilize model-based computational evolution to design an optimized temporal pattern of stimulation that reduced the average stimulation frequency of DBS and preserved efficacy (thereby reducing the energy requirement for stimulation and consequent risks associated with frequent IPG replacements). The model-based computational evolution may utilize an improved cost function. A model of the basal ganglia may be coupled with a genetic algorithm and used in the design of an optimized stimulation pattern. Genetic algorithms (GA) are well suited to this problem, where there is a highly complex, non-linear relationship between the input (stimulus pattern) and output (neural activity), and the GA operates analogously to evolution through natural selection, where the organisms are the temporal patterns of DBS. The GA is used to design a stimulation pattern that minimized average stimulation frequency and error index (EI), a model-based proxy for symptoms (see FIG. 1A). The EI is a measure of the fidelity of information transmission through the thalamus under modulation by the output of the basal ganglia, and is used here as a proxy for parkinsonian bradykinesia (FIG. 1B). In other embodiments, the EI could be used as a proxy for any disease, condition, symptom or the like for which electrical stimulation is applied to develop an efficient if not maximized electrical stimulation temporal pattern. The fitness of each stimulation pattern is evaluated with a cost function that incentivized reducing both EI and the average stimulation frequency. Patterns with greater fitness are more likely to pass their genes (pattern characteristics) on to the next generation of patterns (FIGS. 1C and 1D). The cost of the best stimulation pattern in each generation declines monotonically across generations, while the median cost across the population in each generation declines more slowly (FIG. 1E). The resulting optimal pattern in this specific embodiment has an average frequency of 45 Hz and reduced the EI in the model by almost 98 percent relative to a 45 Hz, constant-frequency stimulation (FIG. 1F). The figures presented are merely exemplary. To determine the optimal pattern of electrical stimulation for a different disease, condition or symptom one need only follow the above representative process replacing the applicable proxy described above with a proxy applicable to such disease, condition or symptom.

Figure 1B:
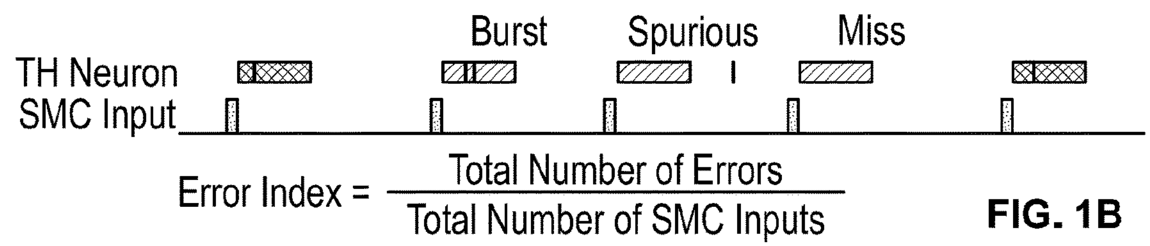
Figure 1C:
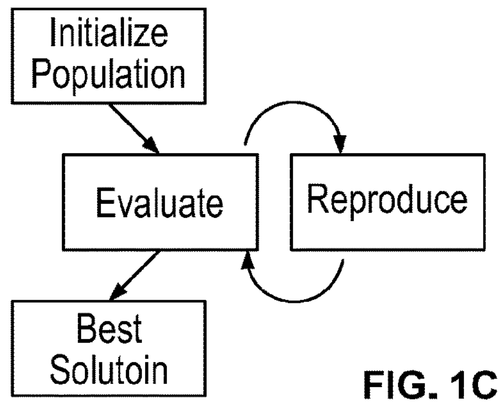
Figure 1D:
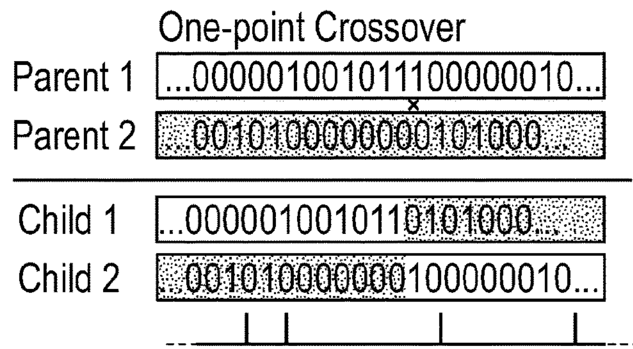
Figure 1E:
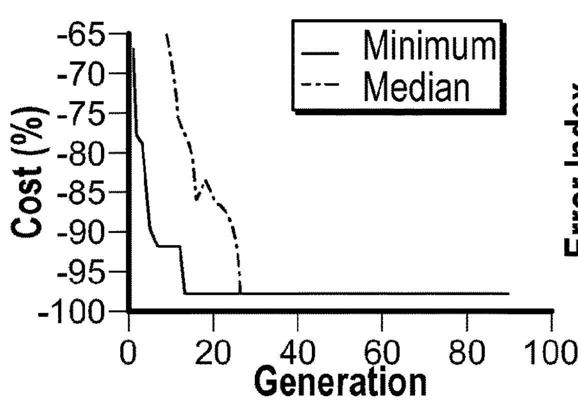
Figure 1F:
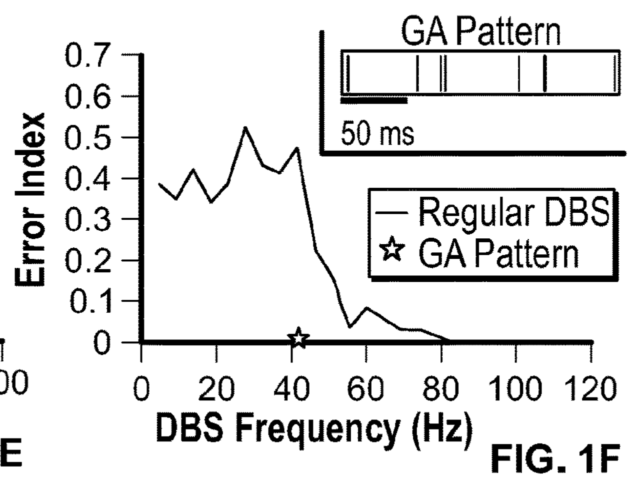

Turning to FIGS. 1A through 1F, they illustrate various aspects of model-based design by computational evolution of an optimized temporal pattern of DBS. These are merely exemplary and not limiting. The same process may be utilized to treat any disease, condition or symptom through electrical stimulation by determining the optimal temporal pattern of stimulation for such disease, condition or symptom. In FIG. 1A, a computational model of the parkinsonian basal ganglia is illustrated that includes the external globus pallidus (GPe), sub-thalamic nucleus (STN), internal globus pallidus (GPi), thalamus (TH), and an input action potential train from the sensorimotor cortex (SMC). Applied currents (→) representing inputs to GPe, GPi, and STN are modeled ($I_{app,GPe}$, $T_{app,GPi}$, and $I_{app,STN}$); GPe primarily receives inputs from striatal neurons expressing inhibitory D2-type receptors ($D2^-$), while GPi primarily receives inputs from striatal neurons expressing excitatory D1-type receptors ($D1^+$). Excitatory and inhibitory synapses are depicted using forked (Y) and circular (•) terminations. FIG. 1B illustrates one example of an error index (EI), a measure of the fidelity of thalamic neuron response to SMC input. If a thalamic (TH) neuron does not fire an action potential within 25 ms of a SMC input, an error occurs. There are three types of errors: misses, bursts, and spurious. EI is defined as the total number of errors divided by the total number of SMC inputs. FIG. 1C is an illustration of a diagram of a genetic algorithm (GA). A random population of stimulation patterns is initialized. Subsequent generations of patterns are created by using principles from biological evolution and evaluated according to the cost function. After convergence, the pattern with the lowest cost (GA) is selected to be tested in the hemi-parkinsonian rats and human patients. FIG. 1D is an illustration of representation of stimulation patterns. Defined by binary strings, new patterns are created by one-point crossover. FIG. 1E is an illustration of trajectory of convergence to a GA pattern of stimulation during successive generations of modeling. FIG. 1F is an illustration of an error index of standard (black line) and the optimized GA (red star) stimulation pattern. The insert of FIG. 1F is a 200-ms segment of the repeating GA pattern of stimulation.

Figure 2A:
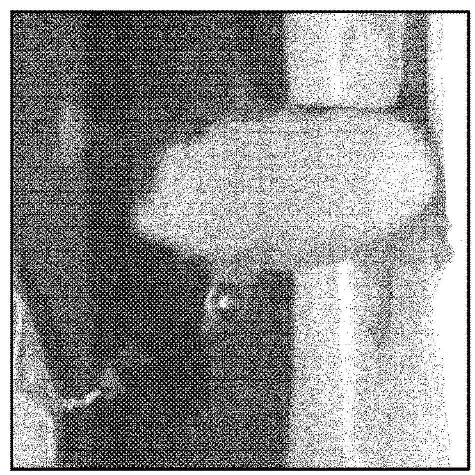
FIGS. 2A through 2D illustrate the effects of temporal patterns of STN DBS on motor symptoms in hemi-parkinsonian rats.
Figure 2B:
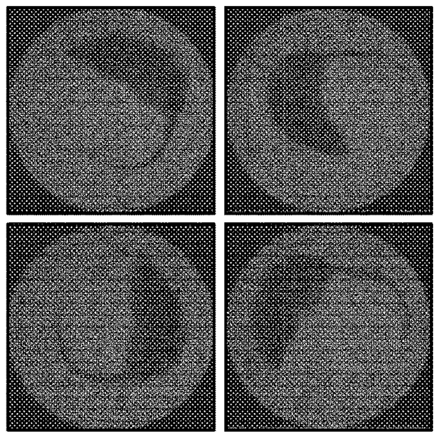

Efficacy of Optimized GA Pattern of Stimulation in Hemi-Parkinsonian Rats: The optimized pattern of DBS (GA) is compared to DBS-off (baseline), 45 Hz DBS, and 130 Hz DBS in hemi-parkinsonian rats by using two well-established measures of parkinsonian symptoms that exhibit DBS frequency-dependent effects that parallel those observed in clinical studies: the bar test to assess akinesia (see FIG. 2A) and methamphetamine-induced circling to assess locomotor behavior (see FIG. 2B).

There is a significant effect of stimulation condition on time on the bar, and all patterns of stimulation reduced time on the bar compared to baseline. Both 130 Hz and GA significantly reduced time on the bar compared to 45 Hz (see FIG. 2C). Similarly, there is a significant effect of stimulation condition on circling rate, and all patterns of DBS reduced circling rate compared to baseline. High-frequency (130 Hz) DBS reduces circling rate more completely than does 45 Hz or GA. Although in humans with PD, less than 50 Hz DBS is ineffective and 130 to 185 Hz is used for treatment, in 6-hydroxydopamine (6-OHDA) lesioned rats DBS at 30 to 75 Hz is at least partially effective at treating parkinsonian symptoms including methamphetamine-induced circling, akinesia, and reduces open field mobility. Thus, in parkinsonian rats, the optimized GA stimulation pattern performs better than the partially effective standard 45 Hz, although 130 Hz DBS performs better than either. There is no effect of stimulation condition on normalized distance traveled (see FIG. 3); the results from this control indicate that the reductions in circling rate achieved by DBS (see FIG. 2D) do not simply reflect decreases in overall movement or activity, but rather demonstrate a resolution of the pathological circling behavior.

Figure 2C:
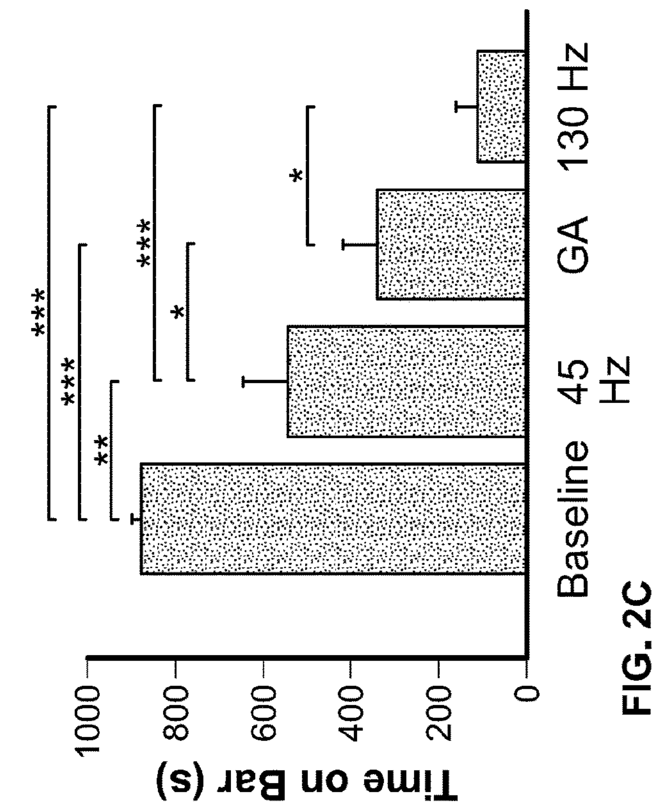
Figure 2D:
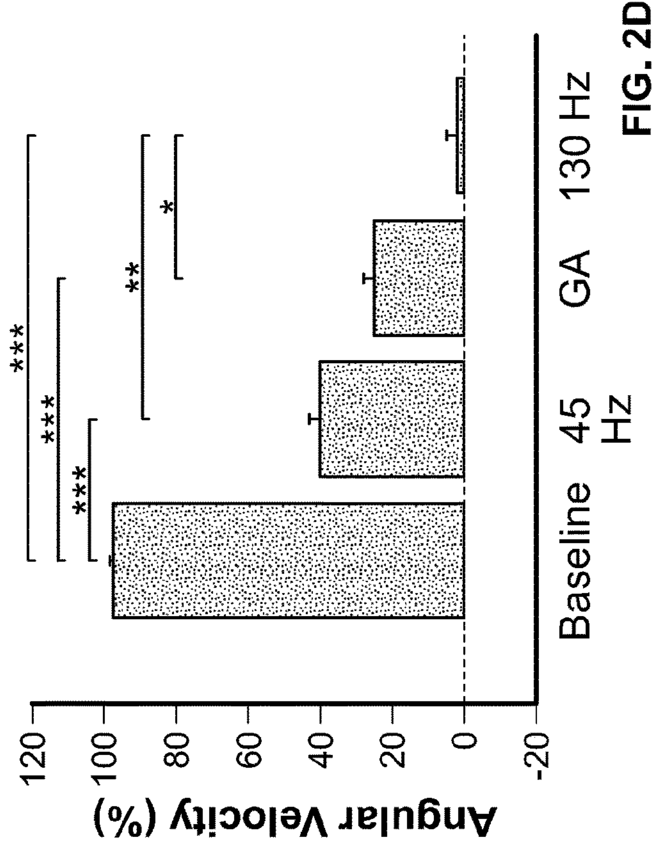
Figure 3:
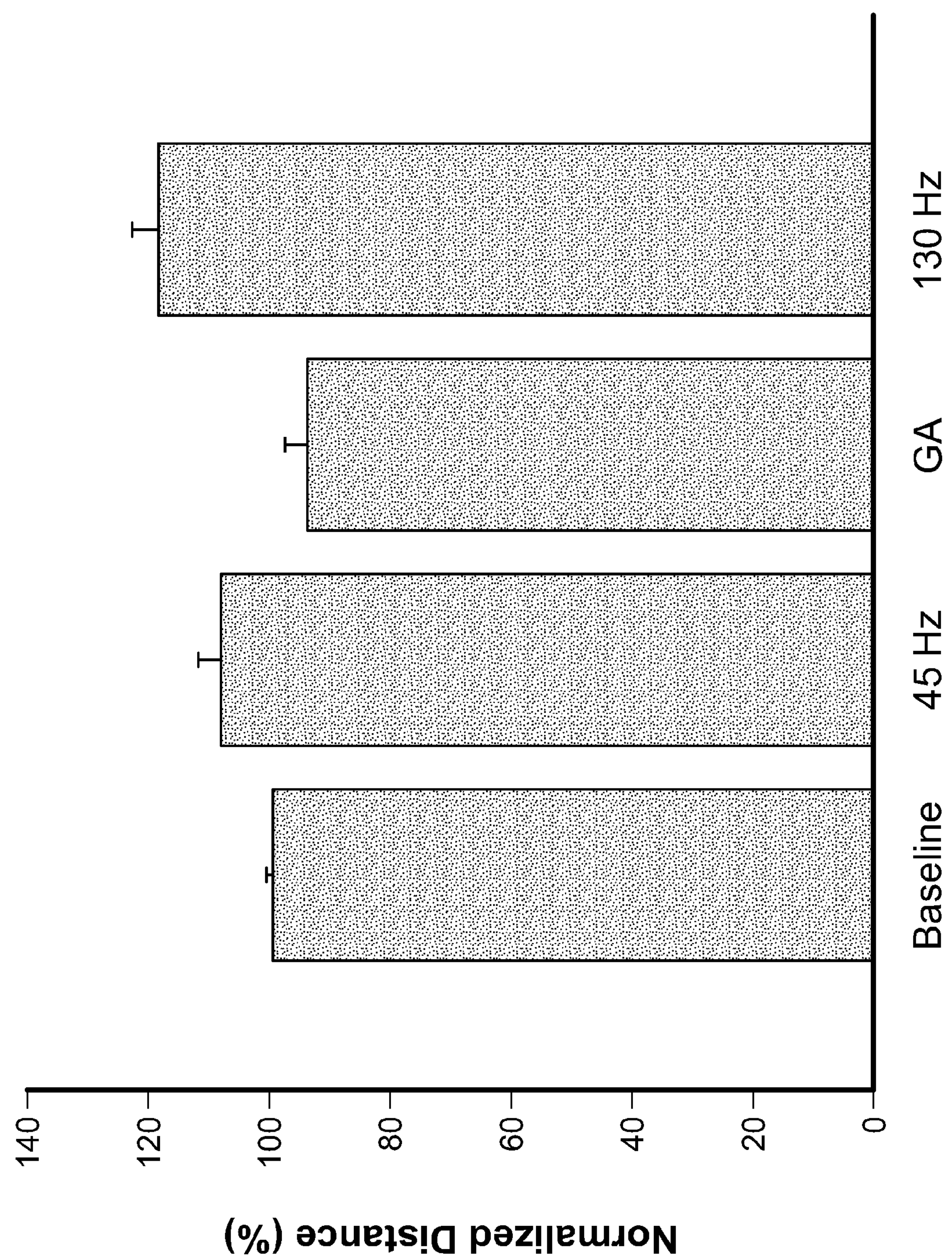
FIG. 3 is an illustration of the effect of stimulation pattern on total distance traveled during the methamphetamine-induced circling task.

As noted above, FIGS. 2A through 2D illustrate the effects of temporal patterns of STN DBS on motor symptoms in hemi-parkinsonian rats evaluated using the bar test (see FIG. 2A) and methamphetamine-induced circling (see FIG. 2B). FIG. 2C illustrates the total time (mean±sem) spent on bar in all three stimulation conditions in the bar test (n=9). Rats are akinetic and unable to dismount from the bar during baseline, but DBS patterns differentially rescue akinesia. FIG. 2D illustrates a normalized circling rate (mean±sem) across stimulation conditions (n=13). The pathological ipsiversive circling rate is differentially reduced by the DBS patterns. Repeated measures analysis of variance (RM-ANOVA) reveal a significant effect of stimulation condition on time on the bar (p less than 0.0001) and normalized angular velocity (p less than 0.0001). Fisher's protected least significant difference (PLSD) test is used to perform post-hoc comparisons between stimulation conditions (*p less than 0.0001; p less than 0.001; *p less than 0.05).

Efficacy of Optimized Pattern of Stimulation:

The system and method of the present invention quantifies unilateral motor symptoms—either bradykinesia or tremor—on the more affected side in subjects with STN DBS for PD (see Table 1) undergoing IPG replacement surgery during DBS off (baseline), temporally regular 185 Hz DBS (185 Hz), temporally regular 45 Hz DBS (45 Hz), and the optimized GA pattern with an average frequency of 45 Hz (GA).

TABLE 1

Subject information.

| | Subject | Age/ Sex | Hemi- sphere/ Target Tested | Electrode Contacts$^{a,b}$ | AMP (V)$^{b}$ | PW (μs) | FREQ (Hz) | PD medications 12 hours prior to surgery |
|---|---|---|---|---|---|---|---|---|
| Bradykinesia | B1 | 55/M | Right/SIN | $1^-/2^-/0^+$ | 3.9 | 60 | 185 | none |
| | B2 | 59/M | Right/STN | $0^-/1^-/2^+$ | 3.5 | 60 | 185 | none |
| | B3 | 69/F | Left/STN | $1^-/2^-/3^+$ [$1^-/2^-/C^+$] | 2.6 | 60 | 185 | 10 mg carbidopa 100 mg levodopa |

TABLE 1-continued

Subject information.

| | Subject | Age/ Sex | Hemi-sphere/ Target Tested | Electrode Contacts[a,b] | AMP (V)[b] | PW (μs) | FREQ (Hz) | PD medications 12 hours prior to surgery |
|---|---|---|---|---|---|---|---|---|
| | B4 | 64/M | Right/STN | $1^-/2^-/3^+$ [$1^-/2^-/3^-/C^+$] | 4.0 [1.9] | 60 | 185 | 25 mg carbidopa 250 mg levodopa |
| Tremor | T1 | 69/M | Right/STN | $1^-/2^-/3^-/0^+$ [$1^-/2^-/3^-/0^+$] | 3.5 [3.8] | 90 | 135 | none |
| | T2 | 66/M | Right/STN | $2^-/C^+$ [$2^-/C^+$] | 2.2 [3.3] | 60 | 130 | none |
| | T3 | 66/M | Right/STN | $1^-/2^-/3^+$ [$1^-/2^-/C^+$] | 3.2 | 60 | 180 | none |
| | T4 | 59/F | Left/STN | $1^-/2^-/3^+$ | 2.5 | 90 | 180 | none |

[a]Quadripolar DBS electrode contacts are tunnbered 0 through 3, with 0 most distal and 3 most proximal. Contact polarity denoted by '+' +cathode) and '–' (anode). $C^+$ indicates that the IPG case was used as the anode/current return.
[b]Experimental stimulation parameters are shown. Clinical settings different from the experimental settings are shown in brackets.
Abbreviations: M = male; F = female; AMP = amplitude; PW = pulse width; PREQ = frequency; STN = subthalamic nucleus.

Figure 5:
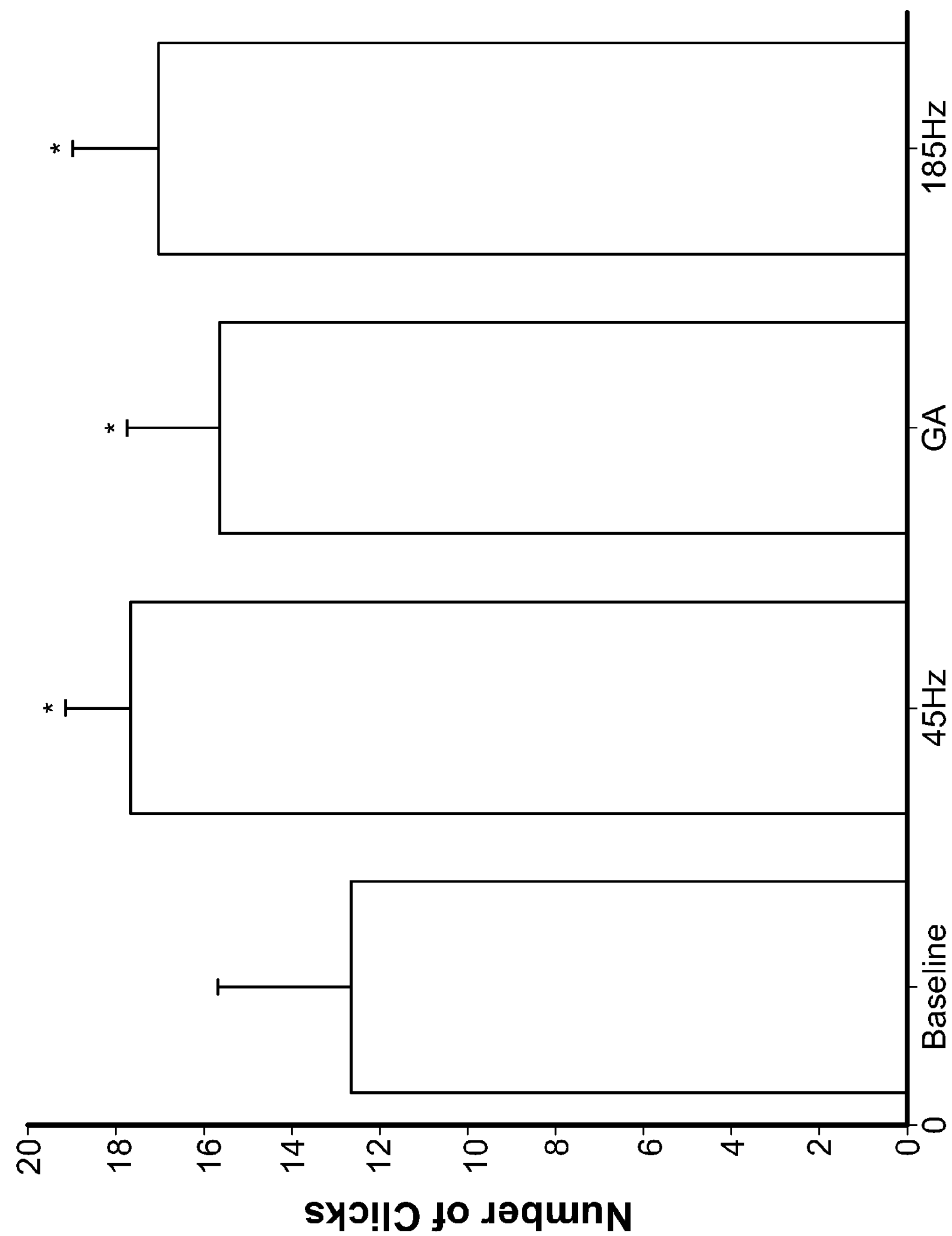
FIG. 5 is an illustration of the effects of stimulation patterns on finger tapping rates in persons with PD and STN DBS.

The present invention is utilized to test bradykinesia-dominant PD subjects (n=4) with an alternating finger tapping task, a quantitative outcome measure strongly correlated with clinical measures of bradykinesia (see FIGS. 4A and 4B). There is a significant effect of stimulation condition on the rate (see FIG. 5) and regularity (see FIG. 4C) of finger tapping. Both GA and 185 Hz significantly improve both the rate and regularity of finger tapping compared to baseline, but 45 Hz only improves tapping rate. Tapping variability is not different between GA and 185 Hz, and both are lower than 45 Hz.

The present invention exploits the correlation between the regularity of finger tapping and Unified Parkinson's Disease Rating Scale (UPDRS) Part III motor examination subscores (to estimate the clinical impact of the different patterns of stimulation. The finger tapping data suggested that 185 Hz reduces UPDRS motor scores by nearly 34 points on average compared to baseline (see FIG. 4D), consistent with previously described effects of DBS, while the GA is predicted to reduce UPDRS motor scores by 31 points. Both GA and 185 Hz are predicted to reduce UPDRS motor scores over 12 points more on average than 45 Hz.

Thus, FIGS. 4A through 4D illustrate the effects of temporal patterns of STN DBS on bradykinesia in persons with PD with FIG. 4A being a diagram of data collection (top) and stimulation schedule (bottom) for evaluation of bradykinesia in PD subjects by using a finger tapping task. Stimulation patterns are applied during the intraoperative experiment with 5 minute on-off intervals, and finger tapping data are collected for 20 seconds thrice during each 5 minute epoch (crosshatched rectangles). The coefficient of variation (CV) of index finger tap durations (Dur) is calculated as the standard deviation (σ) divided by the mean (μ) of the tap durations. FIG. 4B is data from subject B1 across the four experimental conditions. FIG. 4C is the coefficient of variation for index finger tap durations (log-transformed) (mean±sem) across stimulation conditions. RM-ANOVA revealed a significant effect of stimulation condition on regularity of finger tapping (p=0.01, n=4), and Fisher's PLSD test is used to perform post-hoc comparisons between stimulation conditions. GA and 185 Hz DBS significantly improves performance in the finger tapping task relative to baseline (p=0.006 and p=0.004, respectively). Tapping variability is lower for the GA and 185 Hz DBS conditions compared to the 45 Hz DBS condition, but the differences are not statistically significant (p=0.17 and p=0.10, respectively). Individual colored symbols represent individual participants. FIG. 4D illustrates changes in UPDRS III scores (mean±sem) from baseline for various stimulation patterns predicted from the finger tapping task data.

The present invention quantifies unilateral tremor in tremor-dominant PD subjects (n=4) using an accelerometer attached to the dorsum of the hand (see FIG. 6). There is a significant effect of DBS pattern on tremor (see FIG. 6C). Tremor is decreased significantly compared to baseline by GA and 185 Hz. However, 45 Hz does not alter tremor relative to baseline. Further, GA and 185 Hz both significantly decrease tremor compared to 45 Hz.

The present invention utilizes the logarithmic relationship between tremor amplitude and a clinical tremor rating scale (TRS; 0=no tremor to 4=severe tremor) to estimate the clinical and functional impact of the patterns of DBS on tremor. The no-stimulation and 45 Hz conditions reduce the estimated TRS score by less than one point, while GA reduce estimated TRS score by about two points and 185 Hz eliminates tremor (see FIG. 6D). This data indicates that 185 Hz effectively suppresses tremor of all magnitudes, while GA suppresses completely only less-severe tremor. Indeed, GA DBS effectively suppresses tremor in two tremor-dominant PD subjects with a mean baseline tremor power of 61.5 $m^2/s^4$, but does not suppress tremor in two subjects with a mean baseline tremor power of 153 $m^2/s^4$.

Thus, FIGS. 6A through 6D illustrate the effects of temporal patterns of STN DBS on tremor in persons with PD where FIG. 6A illustrates a tremor that is quantified in subjects with tremor-dominant PD by attaching an accelerometer to the dorsum of the hand. The power spectral density (PSD) is estimated and summed across the three orthogonal accelerometer axes ($A_x$, $A_y$, $A_z$), and tremor power ($m^2/s^4$) is calculated by integrating the summed PSD (ΣPSD) with respect to frequency (df) in the 2 to 20 Hz range. FIG. 6B illustrates tremor data from subject T1 across the four experimental conditions. FIG. 6C illustrates the changes in mean (±sem) log-transformed tremor power (2 to 20 Hz) across stimulation conditions, as compared to the stimulation off condition. RM-ANOVA reveals a significant effect of DBS stimulation condition on tremor ($p<0.0001$, n=4), and Fisher's PLSD test is used to perform post-hoc comparisons between stimulation conditions. GA and 185 Hz DBS significantly reduce tremor relative to baseline (p=0.01 and $p<0.0001$, respectively) and relative to 45 Hz DBS (p=0.048 and $p<0.0001$, respectively). However, 45 Hz DBS does not significantly reduce tremor relative to baseline ($p=0.45$). Individual colored symbols represent individual participants. FIG. 6D illustrates changes in TRS (mean±SEM) across stimulation conditions predicted from accelerometer measurements, compared to baseline.

Optimized Pattern of DBS Suppresses Low Frequency Oscillations:

The system and method of the present invention hypothesizes that the efficacy of temporal patterns of brain stimulation may be related to the suppression of the low frequency oscillatory neural activity that is prevalent in PD and in animal models of PD. Hemi-parkinsonian rats exhibit exaggerated 7 to 10 Hz oscillations that are suppressed in a stimulation frequency-dependent manner, similar to the frequency-dependent amelioration of clinical motor symptoms. In connection with this, field potentials from motor cortex and globus pallidus (GP) ipsilateral to the dopaminergic lesion and STN stimulating electrodes are recorded and quantified suppression of 7 to 10 Hz oscillations in hemi-parkinsonian rats during stimulation with each pattern. Based on this, one observes a significant effect of DBS pattern on 7 to 10 Hz power in both GP and ipsilateral motor cortex. Low frequency oscillatory power is significantly lower during GA and 130 Hz than during 45 Hz in both GP and motor cortex (see FIG. 7).

FIGS. 7A through 7G illustrate the effect of temporal pattern of STN DBS on low-frequency oscillations in the globus pallidus (GP) and ipsilateral cortex (iCTX) of hemi-parkinsonian rats. FIGS. 7A through 7C illustrate power spectra of local field potentials recorded from the GP during regular 45 Hz (FIG. 7A), GA (FIG. 7B), and regular 130 Hz DBS (FIG. 7C). The small, narrow peaks (v) in the power spectra are residual artifacts from amplifier blanking and signal interpolation to minimize the contribution of stimulation artifacts to the recorded signals. FIGS. 7D and 7F illustrate the sum of 7 to 10 Hz power (mean±sem) in the three stimulation conditions in GP (FIG. 7D) and iCTX (FIG. 7F). FIGS. 7D and 7F illustrate that low frequency (7 to 10 Hz) oscillatory power during each DBS pattern is normalized by the pre- and post-stimulation power. FIGS. 7E and 7G illustrate normalized 7 to 10 Hz power (mean±sem) in the three stimulation patterns in GP (FIG. 7E) and iCTX (FIG. 7G). RM-ANOVA reveals a significant effect of DBS condition on normalized 7 to 10 Hz power in GP ($p=0.0035$, $n=3$) and iCTX ($p=0.0003$, $n=3$), and Fisher's PLSD test is used to perform post-hoc comparisons between stimulation conditions. GA and regular 130 Hz DBS significantly reduces normalized 7 to 10 Hz power compared to regular 45 Hz DBS in GP ($p=0.0021$ and $p=0.0026$, respectively) and in iCTX ($p=0.0002$).

Human subjects with PD exhibit exaggerated β-band oscillations (30), and improvements in bradykinesia after dopamine therapy and high frequency DBS are associated with reductions in this β activity. The β-band power across stimulation patterns in six human subjects undergoing surgical implantation of the DBS lead in STN for PD is quantified. β-band power is prominent in the DBS off condition and is suppressed differentially by the stimulation patterns (see FIG. 8A). GA and 130 Hz both significantly suppresses β-band power compared to the off condition and 45 Hz (see FIG. 8B). β-power from this cohort of DBS implant subjects is correlated, across DBS conditions, with the finger tapping performance that is measured in the earlier cohort of subjects undergoing motor symptom measurement (see FIG. 8C).

Figure 8A:
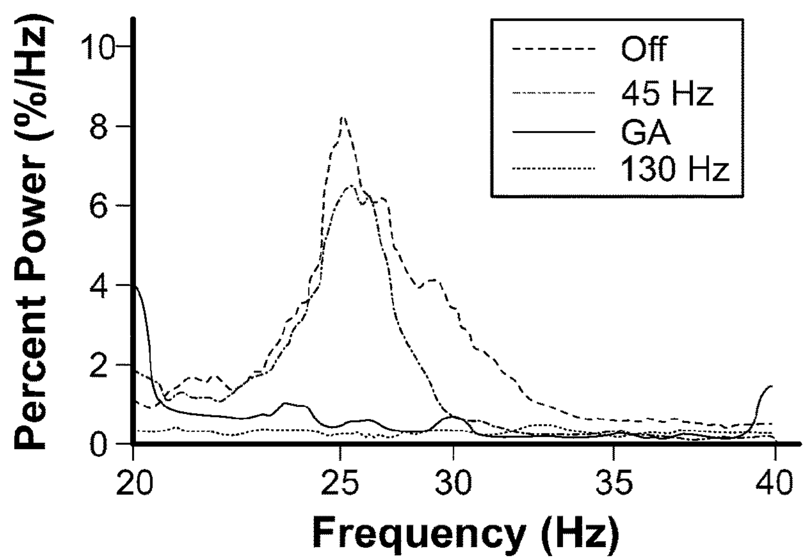
FIGS. 8A through 8C illustrate the effect of temporal pattern of DBS on β band oscillatory activity in the STN of persons with PD.
Figure 8B:
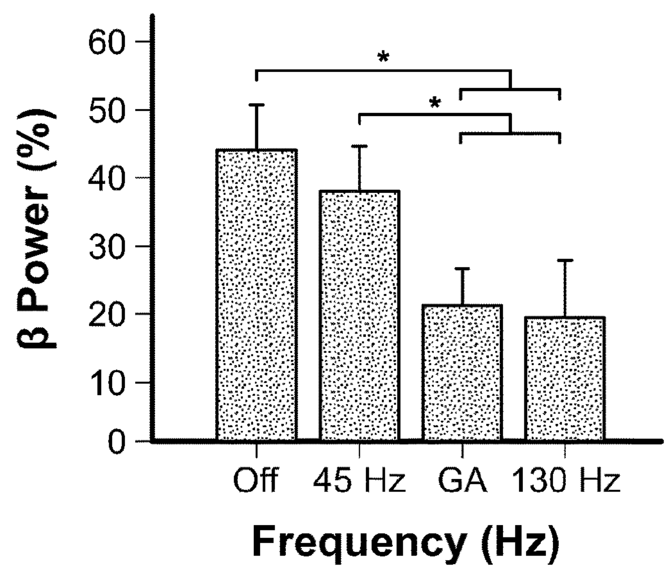
Figure 8C:
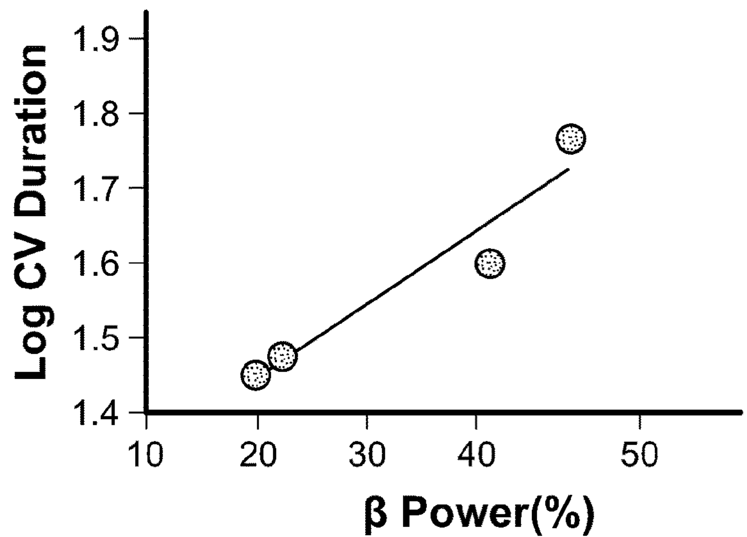

FIGS. 8A through 8C illustrate the effect of temporal pattern of DBS on β band oscillatory activity in the STN of persons with PD with FIG. 8A illustrating spectra estimated for the three stimulation conditions. Local field potentials recorded from the STN during DBS lead implant surgery. FIG. 8B illustrates the percent β power quantified across stimulation conditions and averaged across subjects ($n=6$; mean±sem). Power in the beta range (typically 20 Hz to 33 Hz) is integrated and compared across stimulation conditions. RM-ANOVA reveals a significant effect of DBS condition on percent β power ($p=0.0007$), and Fisher's PLSD test is used to perform post-hoc comparisons between stimulation conditions. GA DBS and 130 Hz DBS significantly suppress beta power compared to DBS off ($p=0.0008$ and $p=0004$, respectively) and 45 Hz DBS ($p=0.0092$ and $p=0.0041$, respectively). FIG. 8C illustrates the relationship between percent β power and finger tapping task performance (as measured by log CV duration). The best fit line is shown for log CV duration data from FIG. 3C and the percent 13 power data from panel B.

In light of the above, one embodiment of the present invention combines model-based optimization using computational evolution, preclinical experiments in a parkinsonian animal model, and translational experiments in patients with PD to design and evaluate a new temporal pattern of stimulation, e.g., DBS. The optimized temporal pattern achieves efficacy at a low average frequency that is not effective during non-patterned stimulation. Further, the suppression of low frequency oscillations by both the GA and high frequency DBS suggests a potential therapeutic mechanism shared by effective stimulation, whether patterned or un-patterned. Although there is a correlation between β-frequency power and bradykinesia and β activity is suppressed by DBS and levodopa, β activity may not correlate consistently with motor symptoms and changes in β activity are inconsistent across patients.

The present invention is utilized to design and evaluate a procedure to optimize temporal patterns of neural stimulation to maximize simultaneously efficacy and efficiency. The pattern of DBS emerging from the present invention's computational evolution method is only optimal for the specific model and cost function that are used. Additionally, the present invention makes it possible to improve further the efficacy and efficiency of non-regular patterns of stimulation in a patient-specific manner, for example, by building patient-specific models for optimization.

Figure 9:
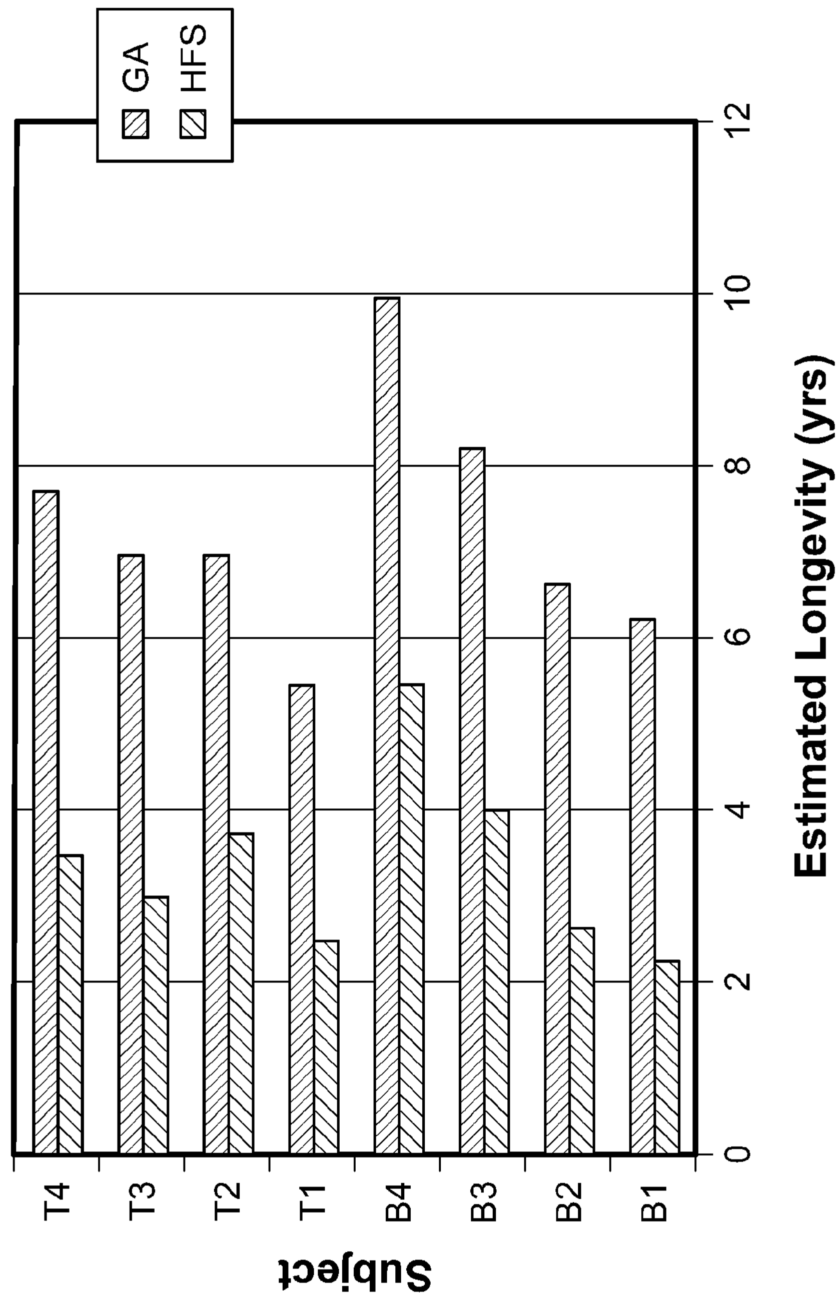
FIG. 9 is an illustration of estimated battery longevity by subject with GA DBS compared to clinical parameters.

The present invention's optimized temporal pattern of stimulation that produces symptom relief at a lower average frequency has advantages over conventional high frequency DBS (typically 130 to 185 Hz). IPGs (or external pulse generators) delivering the optimized low frequency pattern of stimulation consume less energy, and reduced energy consumption translates into longer battery life and less frequent IPG replacement. It is estimated that the subjects included in this study would achieve an average of 3.9 years of additional battery life if they had used GA DBS instead of their current high frequency DBS (see FIG. 9). In contrast to previous work using DBS at frequencies less than 100 Hz, the stimulation pulse width and amplitude utilized in connection with the present invention are identical to those used for high frequency stimulation, but the optimized temporal (GA) pattern delivers substantially less electrical energy. Lower average stimulation frequencies may also decrease stimulation side effects, as there is an inverse relationship between stimulation frequency and side effect intensity. However, the nature of the intraoperative testing environment precluded assessment of the effect of stimulation pattern of the side effects produced by DBS. Intermittent DBS may be an alternative approach to reduce stimulation energy, but intermittent thalamic stimulation in patients with essential tremor and intermittent STN DBS in patients with PD are less effective than constant stimulation.

Tremor reduction after onset of DBS and recovery after cessation of DBS occurs within seconds, and approximately 85 percent of the reduction of bradykinesia occurs within 2 minute of starting DBS. The short trials of the present invention may have underestimated the changes in symptoms, but this underestimation would be similar across stimulation patterns and therefore allow valid relative comparisons.

The GA DBS performance is equivalent to high frequency DBS in the bradykinesia-related finger tapping task. The predicted changes in UPDRS motor sub-scores produced by stimulation with the GA pattern are equivalent to those produced by 185 Hz, comparable to those in large, randomized trials of DBS, and exceed the threshold for large clinically important differences. This suggests that GA and 185 Hz DBS will provide functionally similar alleviation of motor symptoms and clinically meaningful symptom improvement in bradykinesia-dominant PD patients. The suppression of parkinsonian tremor by GA DBS is somewhat lower than high frequency DBS, suggesting that the present invention's GA DBS pattern may be most appropriate for patients with mild tremor whose primary symptom is bradykinesia. The differential effect on symptoms is consistent with the relationship between EI, used as a model-based proxy for symptoms (disease or condition) during the design process, and bradykinesia observed in previous clinical experiments, and points to an opportunity for optimizing tremor-specific temporal patterns of stimulation by using a tremor-related outcome measure in the computational model.

One of the desired outcomes from a closed-loop DBS system for PD and other neurological disorders is energy savings due to the demand-controlled stimulation. However, the energy required for feedback signal amplification, acquisition, and processing may mitigate possible energy savings from demand-controlled stimulation. As well, this approach is currently hindered by difficulty selecting and recording a symptom-relevant biomarker. Conversely, non-regular temporal patterns of DBS with a low average frequency can provide substantial increases in energy efficiency while bypassing challenges associated with closed-loop systems.

Design:

The aim of the present invention's design is an optimized pattern of DBS (GA) and evaluation of its efficacy and mechanisms in hemi-parkinsonian rats and human subjects with PD. While not wishing to be bound to any one hypothesis, one hypothesis is based on the computational modeling results and is based on the belief that GA would reduce motor symptoms in hemi-parkinsonian rats and human subject with PD to the same extent as regular high-frequency stimulation. Rat behavioral experiments are designed on the basis of power analyses that indicate that ten rats would reveal differences between effective and ineffective stimulation patterns. Enrollment numbers of subjects with Parkinson's disease are projected based on a previous study, but as an exploratory proof-of-concept study and acute intervention, the experimental design does not have explicit stoppage or endpoint criteria. The order of stimulation pattern presentation is randomized across all experiments in rats and humans, and pre-defined quantitative measures of motor performance are used to assess parkinsonian symptoms.

Computation Model of the Basal Ganglia:

Temporal patterns of DBS are designed using a biophysical network model of the basal ganglia and thalamus in the PD state. The model is modified from the original version to represent better neural activity and effects of DBS in PD. The model includes 10 neurons in each of the external globus pallidus (GPe), sub-thalamic nucleus (STN), internal globus pallidus (GPi), and thalamus (TH). The single compartment model neurons receive constant applied currents to represent putative afferent projections that maintained average firing rates consistent with observations in non-human primate models of PD and humans with PD. Thalamic neurons do not receive constant applied currents, but rather receive excitatory pulse inputs intended to represent action potentials from the sensorimotor cortex that arrived at a frequency of 14 Hz (±20 percent). EI is calculated by quantifying the fidelity of the thalamic neurons' responses to these inputs. STN DBS is applied by delivering the pattern of current pulses to each STN neuron. Model simulations are implemented in MATLAB using the forward Euler method with a time step of 0.01 ms and a total simulated time of 50 s.

Stimulation Pattern Design Using a Genetic Algorithm:

A genetic algorithm is an optimization technique based on principles from biological evolution. Patterns of stimulation are encoded using bit strings. Each bit in the string represents 1 ms of time, and the bit's value indicates whether a DBS current pulse is present (1) or not (0) in that epoch. Bit strings contain 200 elements, making each pattern 200 ms long. During initial testing of the GA, the present invention employs an iterative empirical process to identify an appropriate pattern length; longer pattern lengths require many more generations to converge, while patterns that are too short do not result in optimal solutions. To evaluate the DBS patterns in the model, the 200 ms repeating pattern is applied to the STN neurons. After a random initial population of patterns is generated, patterns are evaluated using a cost function and "mated" to create a new population/generation of patterns. After 90 generations, the optimized pattern of stimulation is selected for testing in hemi-parkinsonian rats and patients with PD. The resulting optimal pattern is a repeating vector of inter-pulse intervals, in ms, (2, 50, 16, 4, 52, 19, 2, 48 and 7). Multiple iterations of the optimization algorithm yield highly reproducible temporal patterns. In such embodiments, the aforementioned non-regular simulation pattern may be applied continuously to relieve or reduce the impact of the disease, disorder and/or symptoms.

Each pattern's performance in the computational model was calculated using a cost function:

$$\text{Cost} = 100\% * \frac{EI_{pattern} - EI_{FMC}}{EI_{FMC}},$$

where $EI_{pattern}$ was the pattern's EI, and $EI_{FMC}$ is the EI of the pattern's frequency-matched regular DBS control pattern. Therefore, the cost function is the percent change in EI compared to the pattern's frequency-matched regular DBS control. Since high-frequency regular DBS is highly effective in the model, this cost function incentivized low average frequency patterns of stimulation that suppress errors in the model without explicitly including stimulation frequency in the cost function.

Several lines of evidence support the use of the thalamic relay EI as a model-based proxy for parkinsonian symptoms. Changes in EI as a function of DBS frequency parallel changes in parkinsonian symptoms in 6-OHDA lesioned rats during different frequencies of STN DBS. Similarly, there is a strong correlation between the EI in the model and bradykinesia in persons with PD across different random temporal patterns of DBS. As well, driving the model with GPi activity recorded from parkinsonian non-human primates resulted in high EI, while driving the model with GPi activity recorded during therapeutic DBS resulted in a lower EI. However, these correlations do not necessitate that the EI is a direct measure of motor performance, but rather that there is a strong correlation between the effects of DBS on EI and motor symptoms.

Selective pressure toward more fit patterns is exerted using a roulette wheel parent selection process that gave parents with greater fitness a better chance to mate and pass their genes to the next generation. Patterns are numbered from high to low fitness, and parents are selected by iteratively selecting pairs of numbers from an exponential distribution with mean equal to half the population size. One-point crossover is employed to exchange genetic material between the parents and to generate two offspring patterns of stimulation as part of the next generation of patterns. After the offspring are generated, 0.1 percent of their binary string elements are randomly chosen and switched to mimic genetic mutation. Of the 150 patterns in each generation, 130 are children of the previous generation, 10 are randomly generated immigrants incorporated to add genetic diversity and prevent convergence to local minima, and 10 are the most fit patterns from the previous generation included to assure that optimal patterns were maintained in subsequent generations.

Experimental Testing in Hemi-Parkinsonian Rats:

Experiments are conducted in female Long Evans rats weighing 250 to 350 grams. Platinum-iridium stimulation electrode arrays (2×2, 10 kΩ, MicroProbe, Inc.) are implanted under isoflurane (1 to 3 percent) anesthesia into the STN using stereotactic technique and acute, single channel intraoperative recordings to guide placement (A: −3.6 mm; L: 2.6 mm; V: −6.8 mm, relative to Bregma). The rats are rendered hemi-parkinsonian by injection of 6-OHDA into the median forebrain bundle (A: −2.0 mm; L: 2.0 mm; V: −7.0 mm) via a cannula implanted during the preceding electrode implantation surgery. Desipramine (5 mg/kg, i.p.) and pargyline (50 mg/kg, i.p.) are injected 30 min prior to 6-OHDA lesion to limit its non-specific neurotoxic effects and to maximize the toxic effects of 6-OHDA on dopaminergic neurons.

Four STN DBS conditions (off, 45 Hz, 130 Hz, GA) are evaluated in the hemi-parkinsonian rats using two independent, unbiased, and quantitative outcome measures to evaluate the effects of the temporal pattern of DBS: the bar test and methamphetamine-induced circling. 130 Hz produces maximal reduction of parkinsonian symptoms in rats; however, in contrast to human, increasing the frequency to 185 Hz in rats is more likely to produce side effects including dyskinesia-like movements, and thus lower frequency regular DBS (130 Hz) is used in rats than in humans (185 Hz). All patterns use symmetric, 90 μs per phase biphasic pulses. Stimulation patterns are generated using MATALB scripts and output through an isolated voltage-to-current convertor (A-M Systems, Analog Stimulus Isolator Model 2200) and a custom AC coupler.

Bar Test:

The bar test is a well-established method to quantify akinesia and rigidity in hemi-parkinsonian rats. Rats are injected with haloperidol—a long-acting, non-specific dopamine receptor antagonist—and placed in a clear box containing a bar 10 cm above the floor. The forepaws are placed on the bar and the amount of time before the rat dismounted from this unnatural position is recorded as a measure of akinesia. Non-lesioned and drug-naive control animals dismount the bar in 6.4±2.6 seconds (mean±sem; n=4). Haloperidol doses (0.5 to 5.0 mg/kg, i.p.) are titrated for each rat to a dose that result in the rat staying on the bar for over 5 minutes. Rats are allowed to grip the bar for a maximum of 5 minutes per trial, and trials start every 10 minutes following injection. Three trials are performed to confirm the akinetic effect after haloperidol injection, then 30 minutes of continuous stimulation is applied, and the time required to dismount the bar is recorded and summed across three trials. Experiments testing the different stimulation patterns are carried out on non-consecutive days under the same conditions.

Methamphetamine-Induced Circling: Methamphetamine-induced circling is a well-established method for evaluating locomotor behavior in hemi-parkinsonian rats, and exhibits DBS frequency-dependent rescue of ipsiversive circling behavior that parallels frequency-dependent suppression of motor symptoms observed in clinical studies. Methamphetamine (1.25 to 2.5 mg/kg, i.p.) is administered to the rat, and it is placed in a dark cylindrical chamber. An infrared camera and behavioral analysis software (Clever Sys, Inc.) records and quantifies the rat's rotational asymmetry. Stimulation patterns are presented in randomized order within each block. Four to ten consecutive blocks are run with each rat. Angular velocity and linear speed are quantified for each one-minute epoch of stimulation across patterns and normalized by the angular velocity and linear speed during one minute epochs just prior to and just after the DBS on condition.

Field Potential Recordings in Rats:

Stainless steel screws are implanted over motor cortex and micro-wire electrodes in globus pallidus to record field potentials during DBS (n=3). Platinum-iridium electrode arrays (2×2, 10 kΩ, MicroProbe) are implanted ipsilateral to the STN stimulating electrodes under isoflurane (1 to 3 percent) anesthesia into the GP using stereotactic technique (A: −1.0 mm; L: 3.0 mm; V: −5.2 mm, relative to Bregma). One (1) mm diameter stainless steel screws are positioned juxtaposed to the dura over ipsilateral motor cortex (A: 2.5 mm; L: 2.5 mm (n=2), or A: 4.5 mm; L: 2.0 mm (n=1) relative to Bregma). All recordings of neural activity are referenced to titanium screws inserted through the skull over the cerebellum. After recovering from surgery and the 6-OHDA lesioning procedure described above, the rats are placed in a Faraday cage and neural signals are recorded in the freely moving animal Recordings for each rat take place over the course of 27 minutes: 9 minutes for each stimulation condition divided into 3 minute pre-, during-, and post-stimulation epochs. Field potential recordings are band-passed filtered (0.7 Hz-300 Hz, 2 poles and 4 poles respectively) and amplified 5000× before digital sampling at 2 kHz (Plexon MAP System). Multi-taper spectral estimates are obtained using the Chronux neural signal analysis package (www.chronux.org) and MATLAB.

Figures 10A, 10B:
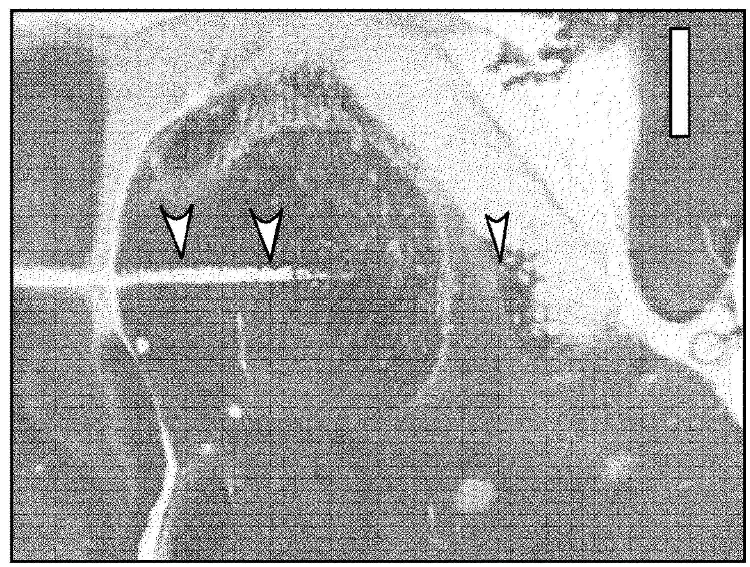
FIG. 10 is an illustration of examples of post-mortem histology.

Histology:

Rats are deeply anesthetized with sodium pentobarbital and killed via intra-cardiac perfusion with 4 percent paraformaldehyde. Their brains are removed, post-fixed, sucrose-protected, and sectioned coronally with 50 μm thickness. Tyrosine hydroxylase immunochemistry is used to confirm effectiveness of unilateral 6-OHDA lesion (see FIG. 10A). Cresyl violet and cytochrome oxidase staining are used to determine electrode placement, and only rats with stimulating electrodes placed in the STN were included in the analysis (see FIG. 10B).

Motor Symptom Evaluation in Persons with Parkinson's Disease:

Inclusion criteria are that the subject is at least three months post DBS electrode implant, capable of performing a simple motor evaluation task, neurologically stable, and capable of understanding the study and consent form. Seventeen subjects consented for the study. Three subjects did not complete the experimental protocol; 5 subjects failed to exhibit better performance during high frequency DBS compared to baseline (DBS off) and are excluded from analysis; one subject's data is discarded due to an inability to confirm that stimulation was delivered; and 8 subjects completed the protocol and are analyzed. Subjects are asked to withhold PD medications for 12 hours prior to surgery, and most (6/8) complied.

Intraoperative Stimulation Protocol and Motor Performance Measurements:

The IPG replacement surgery is performed under local anesthetic (lidocaine). Following removal and disconnection of the depleted IPG, a sterile connection is made between the extension cable and the signal generation equipment. The method of the present invention quantified motor symptoms unilaterally in subjects with PD—either bradykinesia or tremor—across four conditions: off, 45 Hz, 185 Hz and GA. Although prior studies indicate no difference in the effects of DBS on tremor, rigidity or bradykinesia between 130 Hz and 185 Hz, all subjects are programmed to 185 Hz (using their optimal electrode contact pattern) for testing to avoid different control frequencies across subjects. Following completion of the motor symptom evaluation task, the sterile connection between the extension cable and the signal generation equipment is disengaged, and the IPG replacement surgery is completed.

Figure 11:
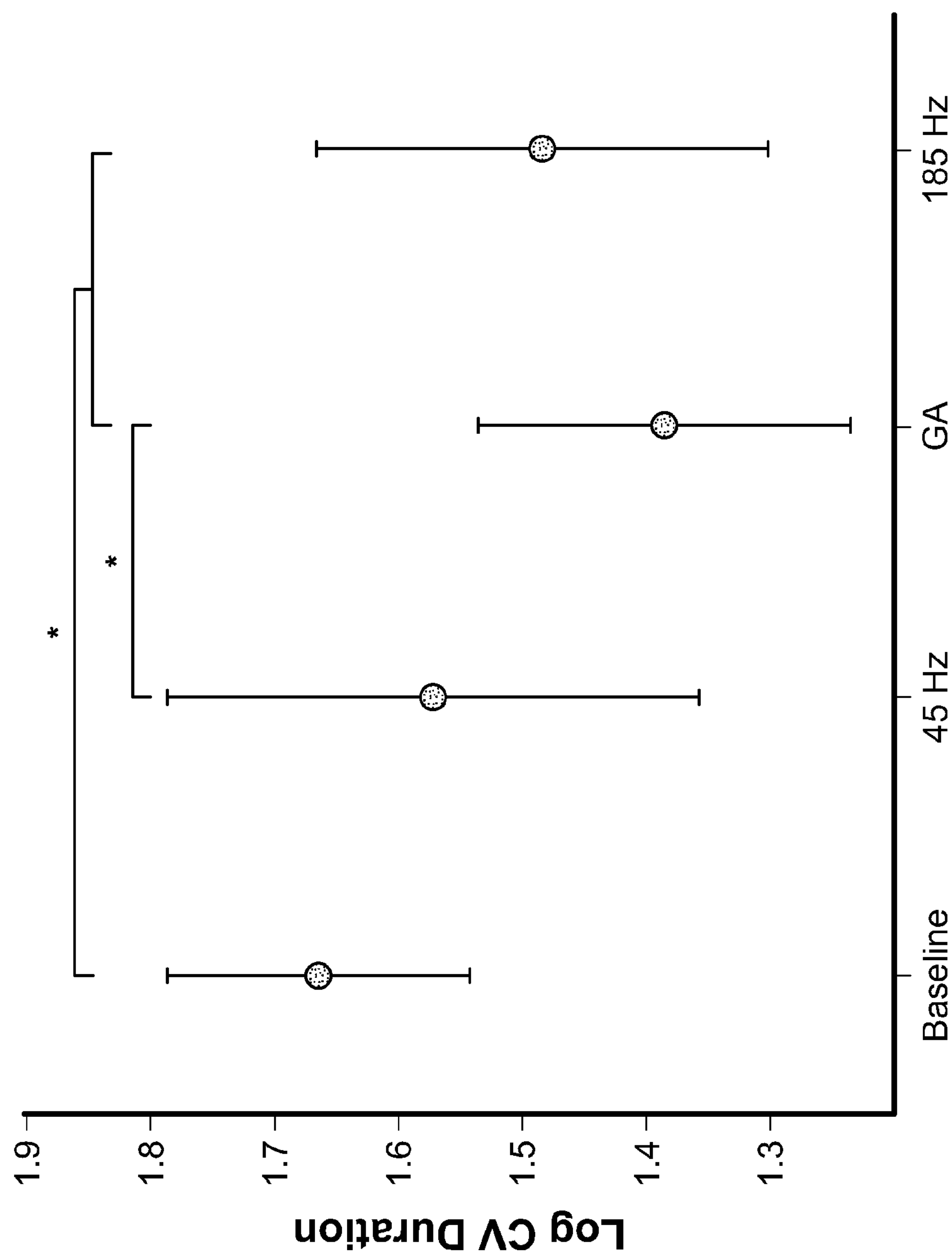
FIG. 11 is an illustration of Finger Tapping Log CV Duration for all three finger tapping trials in each 5 minute epoch.

Bradykinesia is quantified in bradykinesia-dominant PD subjects using an alternating finger tapping task, as the time and physical constraints of the intraoperative environment do not allow the use of the UPDRS to assess outcomes. The hand contralateral to stimulation is placed on a two-button computer mouse, and the subject is instructed to press alternately the buttons as regularly and as rapidly as possible during 20 second trials. Trials are repeated three times during each 5 minute stimulation on or stimulation off epoch, but only the two late trials—starting approximately 210 seconds or 270 seconds into the 5 minute epoch—are analyzed to account for the time course of the effects of DBS on motor symptoms. Analyses including the early trial are included in the Supplementary Material (see FIG. 11). After the baseline condition, the order of stimulation pattern presentation was randomized, and subjects were blinded to the stimulation conditions. The log-transformed coefficient of variation of tap duration is more strongly correlated with the UPDRS motor score than tapping rate, particularly with the bradykinesia sub-score, and was used as the outcome measure for bradykinesia across stimulation conditions. To estimate the clinical impact of the different patterns of stimulation, changes from baseline in Log CV Duration for each patient were scaled by the gain from the significant correlation between UPDRS part III scores and Log CV Duration (80 UPDRS motor points per 0.75 log units) to predict stimulation-induced changes in UPDRS motor examination scores across stimulation patterns.

Experiments in tremor-dominant PD subjects are performed using an accelerometer taped to the dorsum of the subject's hand and a randomized block design with 3 blocks and 1 minute stimulation-on/1 minute stimulation-off pairs. During 20 second trials, the subject is instructed to maintain their hand in a fixed position and refrain from voluntary movements. Signals from the three accelerometer axes (x, y, z) are de-trended using a linear regression based local de-trending algorithm (2 second window, 1 second step size), and power spectra are estimated using Welch's method with a 1 second Hanning window and 50 percent window overlap and summed across all three axes. The peak tremor frequency is between 4 to 5 Hz, and tremor is quantified by integrating the power between 2 to 20 Hz to capture the primary peak as well as the first three harmonics. The change in log-transformed power between 2 to 20 Hz is calculated for each stimulation off/on pair, averaged across blocks, and used as the outcome measure for tremor across stimulation conditions.

To estimate the clinical impact of different stimulation patterns on tremor, changes in five-point TRS scores between off/on stimulation pairs are calculated using:

$$\Delta TRS = \frac{1}{\alpha}\log\left(\frac{T_2}{T_1}\right),$$

where T is tremor amplitude, ΔTRS is the change in tremor rating scale score, and a is an empirically derived linear correlation coefficient (conservatively, $\alpha=0.4$). Tremor amplitude is proportional to the square root of the tremor acceleration power. Therefore, the square root of the 2 to 20 Hz tremor power (described above) is used as a proxy for tremor amplitude and calculated the change in TRS score across patterns.

Intraoperative STN Field Potential Recordings in Subjects with Parkinson's Disease:

Field potentials are recorded from the STN in a separate cohort of nine subjects during DBS lead implant surgery, rather than during IPG replacement surgery, using instrumentation described elsewhere. Three additional subjects consented for the study but withdrew before any intraoperative recordings are performed. All subjects are off medications for Parkinson's disease for at least 12 hours prior to surgery.

The recording instrumentation consists of battery-powered low-noise voltage pre-amplifiers (SR560, Stanford Research Systems) with amplifier blanking in a serial configuration with diode clamps between stages. The relay at the stimulator that disconnected the stimulating contact between pulses, as described in, is removed, and the amplifiers are blanked between 20 μs before through 20 to 500 μs after each DBS pulse, which allowed sufficient gain (2,000 to 10,000×) for field potential recordings without saturation. Although the stimulation waveforms and patterns are the same across all subjects, the duration of stimulation artifacts are variable, apparently as a result of differences in the tissue properties around the electrodes. Therefore, the amplifier blanking duration is tuned individually for each patient.

Symmetric biphasic pulses (90 μs per phase) are delivered through contact 1 or 2 on the DBS electrode lead (whichever is determined to be clinically effective by the attending neurologist), and the stimulation counter electrode is placed on the chest (StimCare Carbon Foam Electrode, Empi). Bipolar recordings are made from contacts 0 and 2 (0+/2−) or contacts 1 and 3 (1+/3−) on the DBS electrode lead, and the implanted cannula served as the recording reference electrode. The 4-contact lead is implanted to place at least 2 contacts (typically 1 and 2 but occasionally 0 and 1) within the T2-positive region considered to be sub-thalamic nucleus on MR imaging (fusing the postoperative CT scan with the pre-operative MRI scan), and electrode tracks are located within the STN with greater than 4 mm electrode track depth of STN. Stimulation is delivered at an amplitude determined to be effective by the neurologist performing the intraoperative assessment (1.5-3.0 V). 45 Hz, GA, and 130 Hz are presented in randomized order for 60 s (n=4) or 300 s (n=5) intervals with intervening intervals of no stimulation. One subject received only 130 Hz before withdrawing and is excluded from analysis.

One objective of the present invention is to quantify the effects of DBS on ongoing β-band activity, as prior data suggest that this activity is correlated with bradykinesia in PD and changes in response to DBS in a manner that paralleled the changes in symptoms. The field potential data are high-pass filtered to remove offset and very slow signal components (2 Hz cutoff, 3 pole Butterworth filter, MATLAB), and the signal is smoothed around the amplifier blanking epoch by linear interpolation from 0.1 ms before to 1.5 ms after the start of the DBS pulse. Evoked compound action potentials are observed in the inter-pulse intervals, and the averaged evoked response is subtracted from the signal to reduce spectral power at the stimulation frequency. Finally, the data are band-pass filtered between 2 to 100 Hz and down-sampled to 400 Hz before spectral analysis (chronux.org). The final 20 seconds or 95 seconds of data from the 60 second and 300 second trials for each condition is selected for spectral analysis (except in one subject who did not complete 300 second of data collection for 130 Hz and a 15 second trial is used in its place). β power is quantified as the percentage of power in a 14 Hz window centered around the β peak in the OFF condition. Two subjects are excluded from analysis because they did not have a prominent β peak in the OFF condition (defined as less than 1 percent/Hz peak power in a β band), leaving six subjects included in the analysis. In most subjects this window coincided well with the high β range (20 to 33 Hz). However, in one subject the β peak is at 14 Hz, and the window is contracted so that it did not include frequencies below 10 Hz.

Figure 12A:
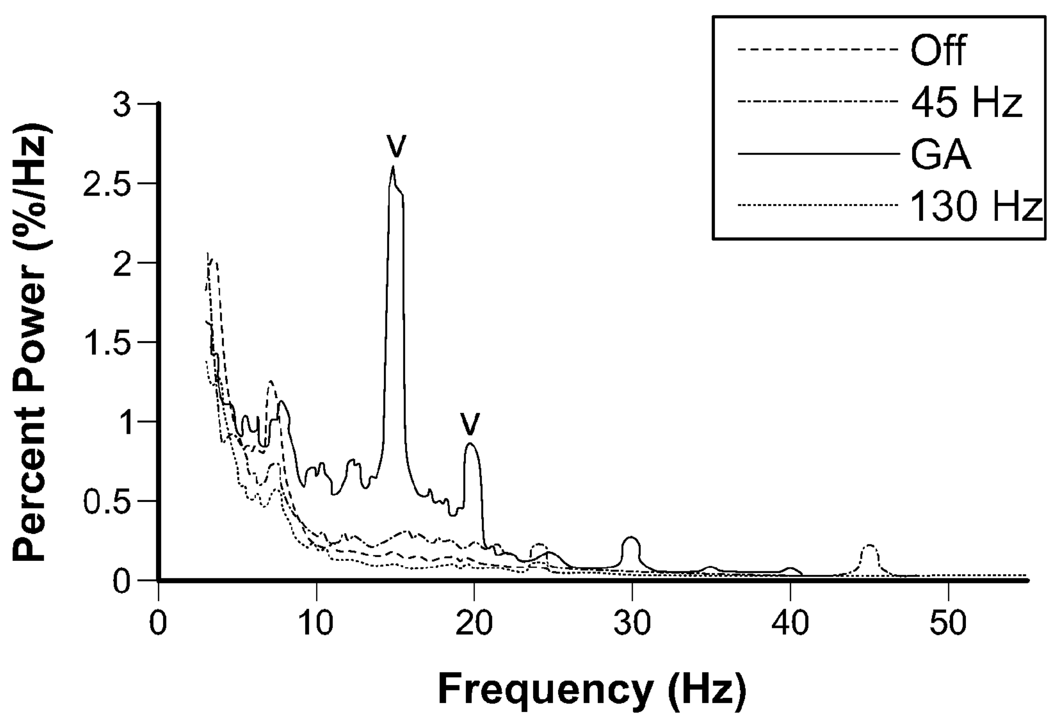
FIG. 12 is an illustration of example data from a subject that did not exhibit a β peak in the spectrum of field potentials recorded in STN.
Figure 12B:
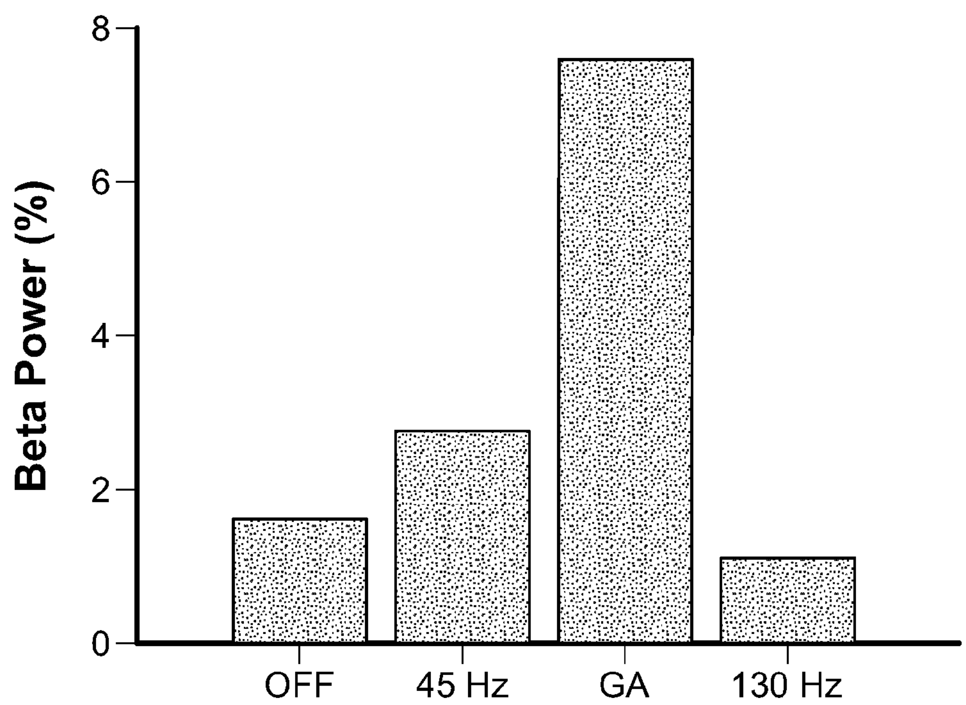

The data processing methods do not artificially reduce β power in the recorded field potentials for the GA condition. In fact, the two subjects that do not have β peaks in their field potential spectra have increased β power due to the GA pattern data processing methods, which introduce small spectral artifacts in the β range (see FIG. 12).

Figure 13:
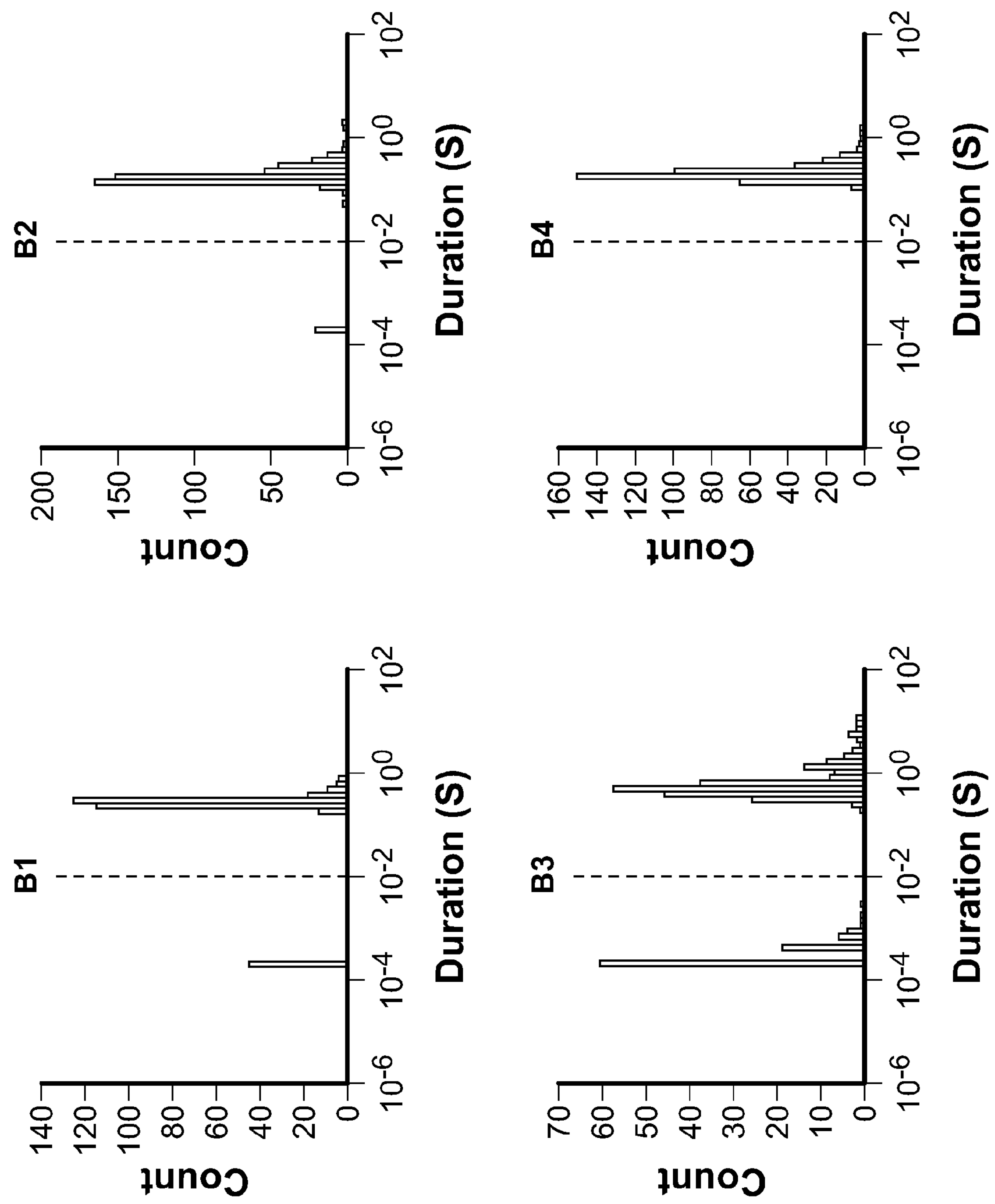
FIG. 13 is an illustration of histograms of tap duration for each subject in the finger tapping task.

Statistical Analysis: Finger-tapping and tremor data are collected using LabVIEW and processed in MATLAB. Technical outliers are removed from the mouse clicking data by discarding extremely short clicks that are artifacts of the computer mouse clicking apparatus (de-bouncing; visual inspection of click duration histograms; see FIG. 13). Statistical analyses are conducted in StatView 5.0.1 for Windows. All rat and human data are analyzed using repeated measures analysis of variance (ANOVA). Post-hoc comparisons between stimulation patterns are performed when indicated by the repeated measures ANOVA using the Fisher's protected least significant difference test (PLSD) with significance defined at $\alpha=0.05$.

Non-Regular, Low Frequency Patterns of Deep Brain Simulation for the Suppression of Neurological Disorder Symptoms:

As noted above, Deep Brain Stimulation (DBS) is an effective therapy for patients with a myriad of neurological disorders. DBS delivers electrical pulses to specific areas of the brain and usually leads to dramatic improvement in the symptoms of the neurological disorder. One aspect of the present invention is directed to increasing the efficacy and/or efficiency of DBS using temporally non-regular patterns of low frequency (less than about 100 Hz) stimulation. Parkinson's disease (PD) is one of the neurological disorders whose symptoms can be treated with DBS. Throughout the description of the present invention, DBS for PD will be used as a non-limiting example of the method and/or system of the present invention as described herein. However, as would be apparent to those of skill in the art upon reading and understanding the present invention, the systems and/or methods described herein are applicable to all types of neurological stimulation including, but not limited to, DBS for a wide range of neurological brain disorders, neurological stimulation for the treatment of a wide range of pain issues, neurological stimulation for the treatment of a bladder issues, etc.

Non-Regular Temporal Patterns of Stimulation:

In one embodiment, the present invention relates to the use of low frequency (less than about 100 Hz) non-regular patterns of DBS, or other neurological stimulation, for the treatment of symptoms of neurological brain disorders, or even other neurological disorders be they brain-based or not. A non-regular temporal pattern of stimulation is a sequence of electrical pulses delivered to neural tissues whose intervals between pulses (the inter-pulse intervals) can vary from one pulse to the next. Regular stimulation simply keeps the inter-pulse intervals the same. Conventional DBS technology delivers regular stimulation at a high frequency (that is frequencies between 100 and 200 Hz).

Rationale for Using Non-Regular Temporal Patterns of Stimulation:

While not wishing to be bound to any one theory, one rationale behind using non-regular patterns of stimulation for the treatment of patients with neurological disorders is that possible mechanisms exist at the cellular and systems level that explain the effectiveness of non-regular patterns of stimulation in connection with neurological stimulation. At a cellular level, the use of non-regular stimulation of the nervous system relies on the possibility that neurons are sensitive to the specific timing of the stimulation pulses. In other words, if the specific timing of the stimulation is important to individual neurons or even a population of neurons it may be advantageous for DBS systems to use non-regular temporal patterns of stimulation to exploit this sensitivity. In the branch of neuroscience concerned with the neural code (i.e., how neurons communicate information with one another) the importance of the timing of inputs to a neuron as it relates to information transfer in the system is a common idea that is termed temporal (or spatiotemporal) coding.

At a systems level, it is thus surprising that a novel non-regular stimulation pattern is more effective than regular stimulation at disrupting or reversing pathological features of a neurological disorder such as Parkinson's disease. For example, a non-regular pattern of stimulation may be able to effectively break up pathological synchronization and oscillations that are common in systems affected by PD.

Exploiting the neural coding by taking advantage of the brain's sensitivity, at any level, to the temporal structure of stimulation makes the technology described herein novel and different than any other stimulation protocol ever developed to treat PD or any other neurological disorder be it brain-related or otherwise.

Design Methodology:

In the non-limiting example of therapeutic DBS for PD given herein the non-regular patterns of stimulation are generated using a computational model of DBS in the STN.

The computation model is then combined with a Genetic Algorithm (GA). Resulting patterns of non-regular, low frequency stimulation can be tested using an intraoperative experiment as described below. There are some important characteristics of the genetic algorithm that should be noted and/or highlighted. First, there is the unique deterministic encoding of patterns of stimulation in the GA such that the GA is directly optimizing the repeating patterns of stimulation, and not optimizing a stochastic process that could create effective non-regular stimulation. Second, there is the use of a cost function in a validated model of neurological disorder pathology. The current GA implicitly forces patterns of stimulation toward lower average frequencies by defining the cost as the percent change in the patterns performance compared to a frequency matched regular DBS control.

Although one embodiment of the present invention utilizes an evolutionary algorithm, namely a Genetic Algorithm (GA), the scope of the present invention and the systems and methods described herein are not limited to just the GAs and/or GA-based approach described herein. Rather, the scope of the present invention shall include all model-based optimization techniques including, but not limited to, other evolutionary algorithms, swarm intelligence algorithms, and other optimization techniques or metaheuristic.

FIG. 1 is an illustration of an exemplary GA-designed non-regular pattern of stimulation for PD. Performance of the non-regular pattern of DBS (right) in the computational model are compared to regular DBS (left). Thus, the scope of the present invention shall not be limited to this particular model of the PD state or to any set of models of neurological disorders. Present or future models of neurological disorders that are treated with DBS, currently or in the future, are candidates for use with the methods and/or systems described in connection with the present invention. Furthermore, the present invention is not limited to a particular pattern or set of patterns generated by the methods described herein.

In one embodiment, the present invention described herein is capable of being implemented in an implantable pulse generator capable of producing specific patterns of the non-regular stimulation.

Supporting Clinical Data:

In one embodiment, the present invention is applied in a non-limiting instance to the treatment Parkinson's disease. A pattern of stimulation is designed using a GA in a computational model of the PD state that preforms much better than frequency matched regular stimulation (see FIG. 1). The GA-designed pattern is applied in human patients during in intraoperative experiments for the first time. These intraoperative experiments are conducted by connecting to the exposed lead of the implanted DBS electrodes during an implantable pulse generator replacement surgery and then delivering the novel pattern of stimulation and a few control patterns. Motor impairment is quantified while delivering the patterns of stimulation using a finger-tapping task (Taylor Tavares et al., 2005). Two patients have completed the experimental study. The 45 Hz average frequency GA-designed pattern of the present invention (GA45) performed similarly to the conventional 185 Hz regular stimulation (Reg185) and better than frequency matched regular stimulation (Reg45). One characteristic of the present invention is that, in one embodiment, it utilizes low frequency (less than about 100 Hz) non-regular DBS to effectively suppress neurological disorder symptoms. Not only does the present invention enable novel methods of designing non-regular patterns of stimulation, but it also enables one to apply such patterns of stimulation to PD as well as other neurological, or neurological-based, disorders.

One non-limiting benefit of the present invention is that it will extend battery life while maintaining a comparable or better level of clinical efficacy. The extended battery life results from a lower average frequency of stimulation. Less current will be delivered over time. Surgeries to replace depleted pulse generators will be needed less frequently and the costs a DBS patient can expect to be associated with a DBS system will be diminished. Furthermore, a lower average frequency of stimulation may lead to fewer side effects from stimulation and a smaller chance of neuronal damage as a result of the stimulation. These factors will lead to increases in the quality of life for patients with DBS.

Typically, the efficacy of DBS deceases with as the frequency of stimulation decreases below 100 Hz. However, unexpectedly the present invention maintains or increases the efficacy of the stimulation while using low frequency stimulation by utilizing a non-regular pattern of stimulation. As discussed above, the non-regular temporal pattern of stimulation takes advantage of the nervous system's sensitivity to the precise timing of the electrical pulses delivered to the nervous system.

Selection or optimization of these non-regular temporal patterns of stimulation can be performed based on neural recordings from a patient. These recordings can be conducted intermittently or on a continuous basis. The problem is, however, that recording neural activity during stimulation is very challenging especially during non-regular patterns of stimulation because—contrary to regular high frequency (greater than 100 Hz) stimulation—there is no guarantee of separation in the frequency domain between neural signals of interest (typically greater than 100 Hz for local field potentials) and stimulation artifacts. Therefore, there is no opportunity to exploit this separation in the frequency domain and suppress stimulation artifacts via filtering (frequency domain solution).

Given the above, the present invention describes in one instance a device and method for obtaining neural recordings during non-regular patterns of brain stimulation using a time-domain solution. Further, the present invention describes applications of these recordings and methods for selection and optimization of temporal patterns of stimulation based on recorded signals. The present invention also describes an implantable pulse generator that is capable of generating and delivering non-regular patterns of stimulation while simultaneously recording neural activity. The implantable pulse generator uses an amplifier-blanking paradigm that briefly grounds the inputs during a short period encompassing the stimulation pulse. This prevents violating the input specifications of the amplifiers (railing the amplifiers), and the short gaps in the data can be overcome with real-time or posts processing analysis methods described below.

The recorded neural activity can be used to monitor the stimulation pattern's performance; control when the stimulation pattern is applied; trigger switches between pre-programmed patterns of stimulation; control interleaving between different stimulation patterns; and/or allow for in vivo optimization of the temporal pattern of stimulation.

The device and methods described herein are not limited to application of any particular type of stimulation. However, the device and methods may be especially useful during non-regular temporal patterns of stimulation because using non-regular patterns of stimulation for the treatment of patients with neurological disorders present a novel and effective method to treat such cases.

At a cellular level, the use of non-regular stimulation of the nervous system relies on the sensitivity of neurons to the specific timing of stimulation pulses. In other words, if the specific timing of the stimulation is important to individual neurons or even a population of neurons, it is advantageous tor DBS systems to use non-regular temporal patterns of stimulation to exploit this sensitivity. In the branch of neuroscience concerned with the neural code (i.e., how neurons communicate information with one another), the importance of the timing of inputs to a neuron as it relates to information transfer in the system is a common idea that is termed temporal (or spatiotemporal) coding.

At a systems level a non-regular stimulation pattern is more effective than regular stimulation at disrupting or reversing one or more pathological features of a neurological disorder such as Parkinson's disease. For example, a non-regular pattern or stimulation disrupts pathological synchronization and oscillations that are common in systems and/or individuals affected by PD. Exploiting the neural coding by taking advantage of the brain's sensitivity, at any level, to the temporal structure of stimulation makes the invention described herein different than any other stimulation protocol ever developed to treat neurological disorders.

Since the primary goal of brain stimulation is to modulate neural activity in the brain, recording neural activity during brain stimulation enables evaluation of stimulation's effects on neural activity. Further, it can guide application, selection, and/or optimization of stimulation parameters, such as the pattern of stimulation, either intermittently or continually.

Neural activity can be recorded from electrodes situated within the brain. The activity may serve as a biomarker for the disease and provide insight into the stimulation parameters that should be used. Here, the present invention is particularly interested in recording neural activity during non-regular stimulation and as such the present invention describes a novel method for achieving these recordings while mitigating the deleterious effects of stimulation artifact.

While not wishing to be bound to any one theory, the efficacy of the non-regular stimulation may depend on its ability to disrupt or otherwise change ongoing neural activity. Further, patterns could be optimized to disrupt certain pathological patterns of neural activity. These therapeutic approaches rely on the ability to record the underlying neural activity, even in the presence of non-regular stimulation. As such, a novel device and methods for achieving this goal is described below along with further applications for these neural recordings. Thus, in one instance the present invention describes the design and application of a novel device and methods capable of recording neural activity during any type of brain stimulation, including non-regular patterns of stimulation.

Figure 14:
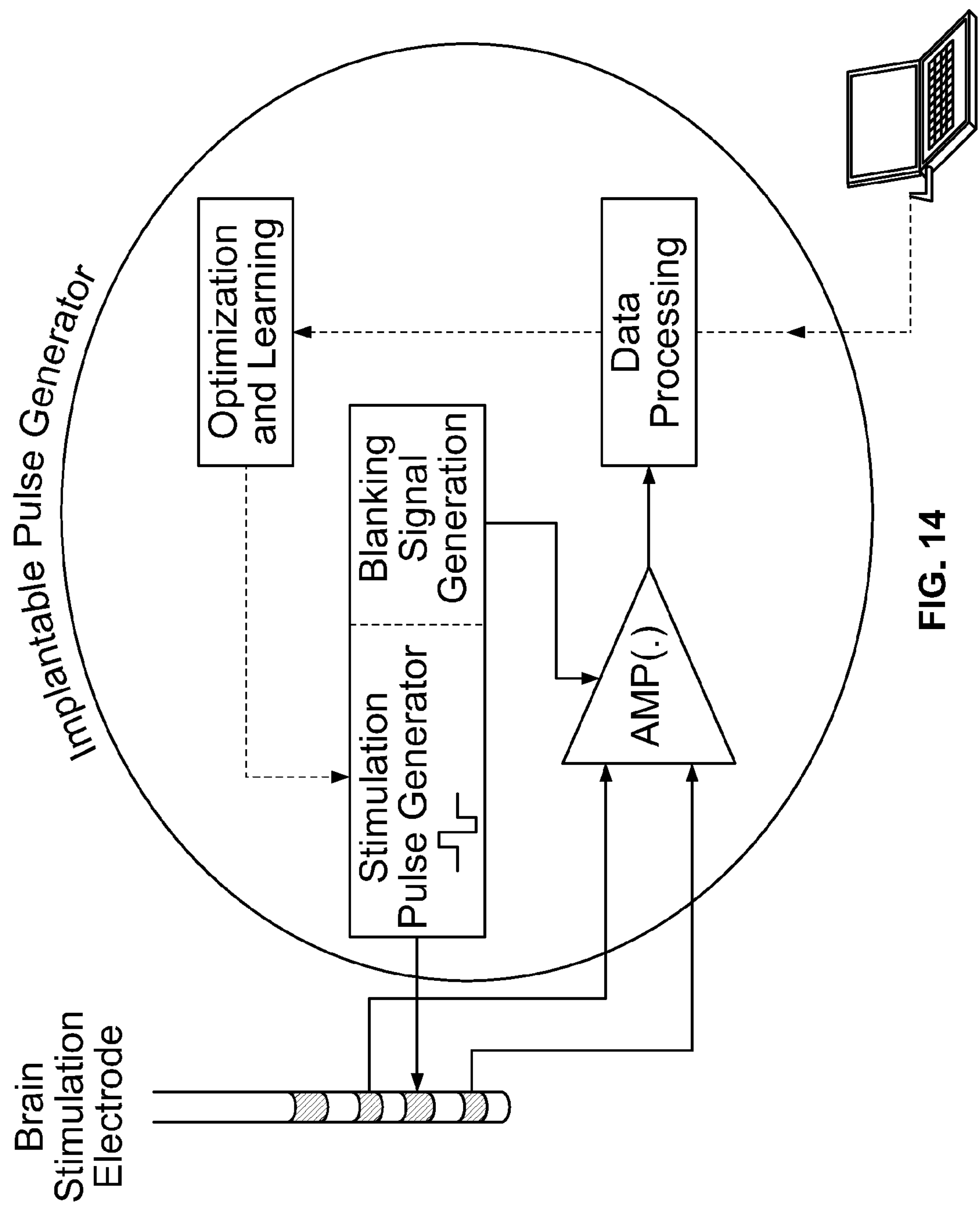
FIG. 14 is a block diagram of an implanting pulse generator according to one embodiment of the present invention.

Turning to FIG. 14, FIG. 14 is an illustration of a simplified block diagram of a system in accordance with one embodiment of the present invention. In this embodiment, the system/device of the present invention includes stimulation pulse generation components that may be coupled to a blanking signal generation module. The blanking signal will be sent to the amplifier/filtering module (AMP9s)) to perform the signal blanking described above. A data processing will perform required data processing (described below). This module will have the ability to communicate wirelessly with devices outside of a patient's body. Dotted lines indicate wireless communication. Dashed lines indicate optional components or connections. The optimization and learning module will use the processed data to control stimulation parameters.

Data Processing Methods:

The present invention utilizes several different data processing techniques to overcome the gaps in the data and still extract signal characteristics of interest. If evoked neural activity is of interest, the gaps are not troublesome and data could be averaged over several stimulation pulses to achieve a measure of the evoked activity. If continuous neural activity is of interest, then the gaps are troublesome, but can be overcome. There are two main approaches: (1) fill in the gaps with modeled data, and (2) work around the gaps while estimating characteristics of interest.

The present invention describes several methods for filling in the gaps with proxy data. One of the simplest techniques is to use linear interpolation within the gaps to join the data points before and after the gaps. This method may introduce bias depending on the signal characteristic of interest. For example, signal spectral characteristics are the preferred signal characteristics in one embodiment, and linear interpolation will introduce bias into the spectrum estimate. Another data processing option is to fill in the gaps with data generated by a model trained on data before and/or after the gap. For example, data generated by an auto-regressive (AR) model will have the same characteristics (spectral and otherwise) as the data the model is trained on, and would produce a good proxy for the real data. Since the data generated by the AR model is not guaranteed to meet the data at the end of the gap, linear interpolation could be used in combination with AR modeling to mitigate the chance of jumps in the reconstructed signal. Note that any method for calculating the AR model (least squares, Burg's algorithm, etc.) could be used, and other types of models could be used to fill in the gaps with data. Lastly, data segments could simply be appended together to eliminate the gaps.

The other data processing approach is to work around the gaps and directly estimate the statistics or signal characteristics of interest. If the spectral content of the recorded signal is of interest, one could bypass reconstructing the data in the gaps entirely and instead train an AR model on the data around the gaps and calculate the power spectrum calculated directly from the model. Several other methods for data analysts exist that will enable working around the gaps in the recorded signal while still extracting the information of interest without introducing bias.

The recorded neural activity can be used purely for monitoring purposes and indicate the efficacy of the stimulation. The recorded activity or summary statistics from the recordings can be downloaded from the device by a health-care provider, company representative, device programmer, or certified research scientists. The recorded neural activity can be used could guide intermittent or continuous modulation of the stimulation parameters. Non-regular temporal patterns of stimulation can be demand-controlled, and stimulation could remain off when not needed (e.g., when asleep). The recorded neural activity can also be used as a trigger or indicator for switching between pre-programmed temporal patterns of stimulation. These different patterns could have different levels of energy efficiency, efficacy, or targeted for different situations (e.g., On/Off medications; tremor/bradykinesia/dyskinesia symptoms, etc.).

The recorded neural activity can be used to guide in vivo optimization or learning algorithm based modulation of the temporal pattern of stimulation. Non-regular patterns of stimulation can be built one inter-pulse interval at a time based on the recorded neural activity. Alternatively, engineering optimization algorithms such as a genetic algorithm can be used to design non-regular patterns of stimulation. Also, a control system can be used to guide the temporal pattern of stimulation. Lastly, machine learning can be used to learn the pattern of stimulation that meets the stimulation objectives (based on the recorded neural activity) most effectively. This can take place in real-time, and real-time reinforcement learning is a good example of an embodiment of this application.

Any in vivo optimization/learning of temporal patterns of stimulation includes safety features to prevent undesired stimulation parameters or uncomfortable side effects. There is defined periods of time when the optimization runs, which could be after the initial electrode and pulse generator implantation or periodically thereafter.

Non-regular temporal patterns of stimulation can be updated and optimized intermittently to meet stimulation objectives (e.g., suppress recorded pathological patterns of neural activity while minimizing energy usage) or changes in the patient or his or her treatment, e.g., different drug treatments. Further, the continuous recording of neural activity allows real-time optimization of the non-regular pattern of stimulation via an automated optimization algorithm incorporated into the implantable pulse generator or through communication (such as wireless communication) from another device (such as a computer, smart phone, etc.) directly to the implantable pulse generator.

The present invention discloses a device that can deliver non-regular temporal patterns of stimulation and simultaneously record neural activity and mitigate the effects of the stimulus artifacts through amplifier blanking and/or stimulation relay. This device can comprise any kind of electrical stimulation device, including, without limitation, an implantable pulse generator or an external pulse generator. Additionally, the present invention utilizes novel data processing techniques for this application that can be used to overcome any bias or error introduced into signal characteristics of interest such as the spectral content. Third, novel applications for using the recorded neural activity as feedback to modulate the stimulation parameters are described. The temporal pattern of stimulation can be a stimulation parameter that is modified, optimized, or otherwise learned based on the recorded neural activity. The application of ECAPs to DBS parameter optimization and closed-loop systems is disclosed. ECAPs indicate how neurons respond during stimulation, and so may better reveal the mechanisms of action of DBS and serve as a reliable feedback signal for brain stimulation.

There is evidence that oscillatory and synchronous neural activity may be the cause of many neurological disorders and may be important to the proper functioning of brain structures. Therefore, the invention described herein is useful to patients with neurological disorders because it can, in some embodiments, provide a feedback signal during any type of stimulation (e.g., non-regular) and enable customization, selection, or optimization of stimulation parameters based on neural activity. Customized stimulation may be more effective and/or efficient than regular high frequency stimulation and/or stimulation patterns. Furthermore, the present invention allows the temporal pattern of stimulation to be adjusted as changes in neural activity occur, perhaps because of disease progression.

Further, a computational model may be calculated using a cost function that is application specific to determine or develop an optimized temporal pattern of stimulation that may be applied to the patient to relieve the disease, symptom or disorder. While the computational model and cost function described above generally applies to PD, a computational model and cost function may be utilized to model any disease, disorder or symptom to which electrical stimulation is applied to treat. While DBS was generally discussed above, the present teachings apply to any kind of electrical stimulation for the treatment of a disease, disorder or symptom. The present teachings achieve an alteration in the mutation method so that it randomly adds, removes, or moves pulses with equal probabilities. It also introduces competitive immigrants, which replaces the standard immigrants method used in other computational models. The present teachings provide a predictive function, in which smart immigrants are created via a pseudo-Bayesian technique that accumulates knowledge about the system over time and uses it to create new genes that are predicted to perform best. The present teachings also relate to the development and incorporation of a jumpstart function that improves the computational model's ability to avoid local minima by intelligently regenerating the population when cost (i.e., fitness) has plateaued. These may all be applied to a computational model related to a specific disease, disorder or symptom to determine the optimal temporal pattern of stimulation to apply to treat the specific disease, disorder or symptom in a manner that is either or both more efficient and efficacious.

For example, a cost function whereby COST=100%*[(Error Index with the Non-Regular Pattern Under Test—Error Index with a Regular Pattern of stimulation with the same average frequency as the Non-Regular Pattern Under Test)/Error Index with a Regular Pattern of stimulation with the same average frequency as the Non-Regular Pattern Under Test] may be utilized with the above to determine the optimal temporal pattern of stimulation. Further, a more generalized cost function may be utilized whereby the cost is given by COST=[A*(power in a specific frequency band of the local field potential or electroencephalogram)]+B*(Average Stimulation Frequency−Target Stimulation Frequency)], or whereby [A/(power in a specific frequency band of the local field potential or electroencephalogram)]+B*(Average Stimulation Frequency−Target Stimulation Frequency)] to develop an optimal temporal pattern of stimulation to treat a specific disease, disorder or symptom.

The optimal temporal pattern of stimulation may applied to any kind of electrical stimulation, e.g., spinal cord stimulation, electrical stimulation for the treatment of pain (such as through peripheral nerves or spinal cord stimulation), occipital nerve stimulation, stimulation for rehabilitation (such as muscles or the like), stimulation for corrective bladder function, stimulation to treat depression, stimulation to treat essential tremor, stimulation for PD or stimulation to treat disease, symptom, or disorder. The process described above may be utilized to determine the optimal temporal pattern of stimulation, which may be applied to treat any disease, disorder or symptom. In some embodiments, as part of the process a proxy for such disorder, disease or symptom may be modeled and then applied as indicated above. The cost function may be applied to determine the optimal temporal pattern of stimulation.

The optimal temporal pattern of stimulation determined above can be applied through an implantable pulse generator, an external pulse generator, a transcranial stimulator, TENS system or the like. The present teachings are not limited to a specific application.

Moreover, instead of or in addition to using a proxy for such disorder, disease or symptom direct feedback from the patient may be utilized. In these embodiments, the patient may be queried for direct feedback regarding how a specific temporal pattern of stimulation is treating the patient's disease, disorder or symptom. This feedback may be applied to the optimization model with the cost function described above and a new optimized temporal pattern of stimulation may be developed. This process may be repeated. This could be done in response to changes in the patient, changes in other treatments being applied to the patient, in response to habituation from the stimulation or any such other reasons. In another embodiment, feedback can be provided by one or more physical/physiological sensors (e.g., accelerometers worn by and/or implanted in a patient; stimulators worn by and/or implanted in a patient; and/or controllers worn by and/or implanted in a patient) where such one or more devices permit real-time refinement of one or more of pulse timing, pattern optimization, algorithm optimization (modified GA or otherwise), or even two or more, or all three thereof.

Still further, sensors may be used with the patient to provide the direct feedback instead or in addition. These can comprise any known such, which may include an accelerometer or accelerometers being attached or otherwise positioned on the patient to sense certain movements. While accelerometers are described, any kind of sensor may be utilized, including, without limitation, thermometers, light meters, movement sensors, passive infrared sensors, NFC, microwave, ultrasonic, vibration, area reflective and dual technology motion sensors may be utilized for example.

An optimization model, such as a GA, with a cost function applied may model treatment of the actual symptom, disease or disorder versus the energy used to treat such through electrical stimulation. All of these components may be tailored to the specific disease, symptom or disorder being treated and may be tailored to the specific patient being treated. Specific personal information regarding the patient may be utilized in the optimization model and cost function to determine an optimized temporal pattern of stimulation applicable to such patient. Certain characteristics of the patient may be provided as a proxy within the optimization model or as direct feedback. This may allow the system to be modified for the patient as he or she is being treated—it allows for real time feedback. The present teachings may be applied to optimize the temporal pattern of stimulation throughout the entire treatment process for the patient.

The temporal pattern of stimulation may comprise a pattern of electrical stimulation of neurons that generates activity—it may modulate influences of neural activity. The stimulation generates action potentials within the neural tissue. These action potentials may treat the applicable disease, disorder or symptom.

Although the embodiments of the present invention have been illustrated in the accompanying drawings and described in the foregoing detailed description, it is to be understood that the present invention is not to be limited to just the embodiments disclosed, but that the invention described herein is capable of numerous rearrangements, modifications and substitutions without departing from the scope of the claims hereafter. The claims as follows are intended to include all modifications and alterations insofar as they come within the scope of the claims or the equivalent thereof.

The terms "component," "module," "system," "interface," "platform," "service," "framework," "connector," "controller," or the like are generally intended to refer to a computer-related entity. Such terms may refer to at least one of hardware, software, or software in execution. For example, a component may include a computer-process running on a processor, a processor, a device, a process, a computer thread, or the likes. In another aspect, such terms may include both an application miming on a processor and a processor. Moreover, such terms may be localized to one computer and/or may be distributed across multiple computers.

What has been described above includes examples of the present specification. It is, of course, not possible to describe every conceivable combination of components or methodologies for purposes of describing the present specification, but one of ordinary skill in the art may recognize that many further combinations and permutations of the present specification are possible. Each of the components described above may be combined or added together in any permutation to define the present system and method. Accordingly, the present specification is intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A method for achieving neural stimulation comprising the steps of:

(A) selecting a neural model based on the nature of a disease to be treated or a neurological stimulation to be achieved;

(B) using the selected neural model to design a stimulation pattern by applying a cost function to the neural model to design the stimulation pattern, wherein the cost function comprises: A*(power in a specific frequency band of a local field potential or electroencephalogram)+B*(average stimulation frequency of the stimulation pattern- target stimulation frequency); and (C) stimulating one or more neurons or one or more neural tissues in an individual using the stimulation pattern designed in Step (B) using a stimulation device.

2. The method of claim 1, wherein the stimulation is deep brain stimulation and the stimulation pattern comprises non-regular pulses.

3. The method of claim 1, wherein the stimulation pattern has a specified average frequency and comprises non-regular pulses.

4. The method of claim 1, wherein the method further includes the steps of:

(D) using feedback from either the individual being stimulated or from the stimulation device to further refine or optimize the stimulation pattern of Step (B).

5. The method of claim 4, wherein the optimization is achieved in real-time by the stimulation device.

6. The method of claim 1, wherein the one or more neurons or one or more neural tissues to be stimulated are in a brain of the individual being stimulated.

7. The method of claim 1, wherein the disease to be treated is Parkinson's disease.

8. The method of claim 1, wherein the method comprises treating one or more pain disorders through the use of neural stimulation.

9. The method of claim 1, wherein the method comprises treating one or more neurological brain disorders, one or more pain disorders, one or more bladder disorders through the use of neural stimulation.

10. The method of claim 1, wherein the method comprises treating one or more neurodegenerative diseases selected from Alzheimer's disease, Parkinson's disease, Huntington's disease, Multiple Sclerosis, amyotrophic lateral sclerosis, Hunter syndrome, mitochondrial encephalopathies, one or more cerebrovascular diseases or conditions, one or more psychiatric illnesses, one or more memory/cognition disorders, epilepsy, one or more neurological-based pain disorders or conditions, migraines, spasticity, one or more types of brain tumors, one or more types of physical trauma, and/or vasospasm.

11. A device for delivering neural stimulation comprising:
- a pulse generator; and
- a processor positioned in the pulse generator, the pulse generator applying an electrical stimulation having a temporal pattern of inter-pulse intervals of 2 ms, 50 ms, 16 ms, 4 ms, 52 ms, 19 ms, 2 ms, 48 ms and 7 ms and repeating the temporal pattern of inter-pulse intervals to treat a disease, disorder or symptom.

12. The device of claim 11, wherein the device is designed to provide deep brain stimulation.

13. The device of claim 11, wherein the electrical stimulation has an average frequency of 45 Hz and comprises non-regular pulses.

14. The device of claim 11, wherein the pulse generator permits optimization of the stimulation patterns based upon patient input.

15. The device of claim 14, wherein the pulse generator permits optimization in real-time.

16. The device of claim 11, wherein the pulse generator stimulates one or more neurons or one or more neural tissues in a brain of an individual.

17. The device of claim 11, wherein the pulse generator treats Parkinson's disease.

18. The device of claim 11, wherein the pulse generator treats one or more pain disorders through the use of neural stimulation.

19. The device of claim 11, wherein the pulse generator treats one or more neurological brain disorders, one or more pain disorders, one or more bladder disorders through the use of neural stimulation.

20. The device of claim 11, wherein the pulse generator treats one or more neurodegenerative diseases selected from Alzheimer's disease, Parkinson's disease, Huntington's disease, Multiple Sclerosis, amyotrophic lateral sclerosis, Hunter syndrome, mitochondrial encephalopathies, one or more cerebrovascular diseases or conditions, one or more psychiatric illnesses, one or more memory/cognition disorders, epilepsy, one or more neurological-based pain disorders or conditions, migraines, spasticity, one or more types of brain tumors, one or more types of physical trauma, and/or vasospasm.

21. A method comprising:
- selecting a neural model based on a disease, symptom or disorder to be treated;
- generating a first non-regular temporal pattern of electrical stimulation;
- applying a cost function to the neural model to modify the first non-regular temporal pattern of electrical stimulation, wherein the cost function comprises: 100%*(an error index with the first non-regular temporal pattern of electrical stimulation−error index with a regular pattern of stimulation with an equal average frequency as the first non-regular temporal pattern of electrical stimulation)/error index with the regular pattern of stimulation with an equal average frequency as the first non-regular temporal pattern of electrical stimulation;
- generating a second non-regular temporal pattern of electrical stimulation having either improved efficacy or efficiency over the first non-regular temporal pattern of electrical stimulation; and
- stimulating one or more neurons or one or more neural tissues in an individual using the second non-regular temporal pattern of electrical stimulation, wherein the second non-regular temporal pattern of electrical stimulation comprises a repeating vector of inter-pulse intervals of 2 ms, 50 ms, 16 ms, 4 ms, 52 ms, 19 ms, 2 ms, 48 ms and 7 ms.

22. The method of claim 21, wherein the second non-regular temporal pattern of electrical stimulation is applied as deep brain stimulation.

23. The method of claim 21, wherein the second non-regular temporal pattern of electrical stimulation has an average frequency of 45 Hz.

24. The method of claim 21, wherein the method further includes the step of:
- using feedback from either an individual being stimulated or from a stimulation device to further refine or optimize the second non-regular temporal pattern of electrical stimulation.

25. The method of claim 21, wherein one or more neurons or one or more neural tissues to be stimulated are in a brain.

26. The method of claim 21, wherein the disease, symptom or disorder to be treated is Parkinson's disease.

27. The method of claim 21, wherein the disease, symptom or disorder being treated comprises one or more neurodegenerative diseases selected from Alzheimer's disease, Parkinson's disease, Huntington's disease, Multiple Sclerosis, amyotrophic lateral sclerosis, Hunter syndrome, mitochondrial encephalopathies, one or more cerebrovascular diseases or conditions, one or more psychiatric illnesses, one or more memory/cognition disorders, epilepsy, one or more neurological-based pain disorders or conditions, migraines, spasticity, one or more types of brain tumors, one or more types of physical trauma, and/or vasospasm.

* * * * *